(12) United States Patent
Hoener et al.

(10) Patent No.: US 9,132,136 B2
(45) Date of Patent: Sep. 15, 2015

(54) PHARMACEUTICAL COMBINATION

(75) Inventors: Marius Hoener, Basel (CH); Susanne Raab, Aesch BL (CH); Celine Risterucci, Mulhouse (FR); Sabine Sewing, Basel (CH)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 13/189,600

(22) Filed: Jul. 25, 2011

(65) Prior Publication Data

US 2012/0028964 A1    Feb. 2, 2012

(30) Foreign Application Priority Data

Aug. 2, 2010   (EP) .................................. 10171560

(51) Int. Cl.
| | |
|---|---|
| *A61K 31/5513* | (2006.01) |
| *A61K 31/422* | (2006.01) |
| *A61K 31/4168* | (2006.01) |
| *A61K 31/455* | (2006.01) |
| *A61K 31/506* | (2006.01) |
| *A61K 31/5377* | (2006.01) |
| *A61K 31/4439* | (2006.01) |
| *A61K 9/16* | (2006.01) |
| *A61K 9/20* | (2006.01) |
| *A61K 9/48* | (2006.01) |
| *A61K 31/40* | (2006.01) |
| *A61K 31/421* | (2006.01) |
| *A61K 31/5375* | (2006.01) |
| *A61K 31/551* | (2006.01) |
| *C07D 413/12* | (2006.01) |

(52) U.S. Cl.
CPC ........... *A61K 31/5513* (2013.01); *A61K 9/1623* (2013.01); *A61K 9/2018* (2013.01); *A61K 9/4858* (2013.01); *A61K 31/40* (2013.01); *A61K 31/4168* (2013.01); *A61K 31/421* (2013.01); *A61K 31/422* (2013.01); *A61K 31/4439* (2013.01); *A61K 31/455* (2013.01); *A61K 31/506* (2013.01); *A61K 31/5375* (2013.01); *A61K 31/5377* (2013.01); *A61K 31/551* (2013.01); *C07D 413/12* (2013.01)

(58) Field of Classification Search
CPC ........... A61K 31/5513; A61K 31/422; A61K 31/4168; A61K 31/455; A61K 31/506; A61K 31/5377; A61K 31/4439; A61K 9/1623; A61K 9/4858; A61K 9/2018
See application file for complete search history.

(56) References Cited

U.S. PATENT DOCUMENTS

| | | | |
|---|---|---|---|
| 2006/0240101 A1* | 10/2006 | Chungi et al. ................. | 424/464 |
| 2009/0036420 A1 | 2/2009 | Galley et al. | |
| 2011/0152245 A1 | 6/2011 | Groebke Zbinden et al. | |

FOREIGN PATENT DOCUMENTS

| | | |
|---|---|---|
| KR | 2007/0022539 | 2/2007 |
| WO | 2006/073886 | 7/2006 |
| WO | 2008/092785 | 8/2008 |
| WO | 2008/098857 | 8/2008 |
| WO | 2010/010014 | 1/2010 |
| WO | 2010/017236 | 2/2010 |
| WO | 2011/057973 | 5/2011 |
| WO | 2011/076678 | 6/2011 |
| WO | 2011076678 | 6/2011 |

OTHER PUBLICATIONS

Branchek et al., "Curr Opin Pharmacol" 3:90-97 ( 2003).
Berry, M. D., "Reviews on Recent Clinical Trials" 2:3-19 ( 2007).
Correll et al., "JAMA" 302(16):1765-1773 ( 2009).
Lindemann et al., "J Pharmacol Exp Ther" 324:948-956 ( 2008).
Sotnikova et al., "Mol Pharmacol" 76:229-235 ( 2009).
Bradaia et al., "Proc Natl Acad Sci USA" 106:20081-20086 ( 2009).
Boulton et al., "Prog Neuropsychopharmacol Biol Psychiatry" 18:17-45 ( 1994).
Bunzow, J. R., "Mol Pharmacol" 60:1181-1188 ( 2001).
Lindemann et al., "Genomics" 85:372-385 ( 2005).
Wolinsky et al., "Genes Brain Behav" 6:628-639 ( 2007).
Borowsky et al., "Proc Nat Acad Sci USA" 98:8966-8971 ( 2001).
Burchett et al., "Progress in Neurobiology" 79:223-246 ( 2006).
Xie et al., "Biochem Pharmacol" 78:1095-1104 ( 2009).
PCT International Search Report mailed Sep. 21, 2011 PCT/EP2011/062772.
Lindemann et al., "Trends Pharmacol Sci" 26:274-281 ( 2005).
Sabelli et al., "J Neuropsychiatry Clin Neurosci" 8:168-171 ( 1996).
The English translation of the Eurasian Office Action, issued on Nov. 27, 2015, in the related Eurasian Patent Application No. 201291476.
Braulke et al., "3-Iodothyronamine: a novel hormone controlling the balance between glucose and lipid utilisation," J. Comp. Physiol B (2008) 178:167-177.
The English translation of the Korean Office Action, issued on Feb. 28, 2014, in the corresponding Korean application No. 2013-7005202.
The English translation of the Japanese Office Action, issued on Apr. 22, 2014, in the corresponding Japanese Application No. 2013-522196.

(Continued)

*Primary Examiner* — Renee Claytor

(57) ABSTRACT

The present invention relates to a pharmaceutical combination for the treatment of schizophrenia and acute manic episodes associated with bipolar disorders, which comprises a compound which is active on a trace amine-associated receptor 1 (TAAR1 agonist) and an antipsychotic drug. This combination can reduce metabolic side effects which appear if using an antipsychotic drug alone.

2 Claims, 14 Drawing Sheets

(56) References Cited

OTHER PUBLICATIONS

The English translation of the Chinese Office Action, issued on Jan. 15, 2014, in the corresponding Chinese application No. 201180036957.6.
The Singapore Office Action, issued on May 28, 2015, in the corresponding Singapore application No. 2013003983.
Uçok et al., "Side effexcts of atypical antipsychotics: a brief overview," World Psychiarty 2008, vol. 7, pp. 58-62.
Henderson et al., "Ziprasidone as an adjuvant for clozapine- or olanzapine-associated medical morbidity in chronic schizophrenia," Human Psychopharmacol. 2009, vol. 24, 3, pp. 225-232.
Kinon BJ et al., "Long-term olanzapine treatment: weight change and weight-related health factors in schizophrenia," J. Clin. Psychiatry, 2001, vol. 62, 2, pp. 92-100, abstract only.

* cited by examiner

PHARMACEUTICAL COMBINATION

PRIORITY TO RELATED APPLICATION(S)

This application claims the benefit of European Patent Application No. 10171560.5, filed Aug. 2, 2010, which is hereby incorporated by reference in its entirety.

BACKGROUND OF THE INVENTION

Schizophrenia is a severe and chronic mental illness, with prevalence estimates ranging from 1.4 to 4.6 per 1000 population.

Schizophrenic disorders and depression are caused by a combination of genetic and environmental factors, which include, for schizophrenia, probable neurodevelopmental abnormalities in gray and white matter structures. Underlying the symptomatic phenomena in both diseases, disturbances in monoaminergic neurotransmission (e.g. serotonin, adrenaline, and noradrenaline) have been proposed.

These pathways are widely present in the CNS and, thus, are potentially capable of influencing many areas involved in emotional processing, cognition, and behavior. Until recently, the excess dopamine hypothesis was the major pathophysiological theory of schizophrenia, based largely on the effectiveness of D2 antagonists in controlling the acute exacerbations of this disease.

Symptoms of schizophrenia, which typically emerge during adolescence or early adulthood, are usually classified as positive, negative or cognitive. Positive symptoms include hallucinations, delusions and severe thought disorganization. Negative symptoms are a group of deficits comprising flat affect, apathy, poverty of speech, anhedonia and social withdrawal. Cognitive symptoms, such as deficits in attention and working memory, are prominent features of the illness and have been identified as powerful predictors of social outcome.

Current atypical antipsychotics are efficacious primarily in the management of positive symptoms, yet have minimal effects on negative symptoms and cognitive function, besides being associated with significant side-effects. Efficacy on cognitive symptoms and improvement of negative symptoms are the highest unmet need in schizophrenia.

First generation drugs are effective but associated with significant incidence of extrapyramidal symptoms, whereas second-generation (atypical) antipsychotics appear to have less incidence of extrapyramidal side-effects and may be more effective in treating cognition but increase the incidence and severity of metabolic syndrome.

A common antipsychotic drug for the treatment of schizophrenia is olanzapine. Olanzapine (Zyprexa) belongs to a drug class known as atypical antipsychotics. Other members of this class include clozapine (Clozaril), risperidone (Risperdal), aripiprazole (Abilify) and ziprasidone (Geodon). Olanzapine binds to alpha-1, dopamine, histamine, muscarinic and serotonin type 2 (5-HT2) receptors.

Olanzapine is approved for the treatment of psychotic disorders, long term treatment of bipolar disorders and in combination with fluoxetine for the treatment of depressive episodes associated with bipolar disorders and for the treatment of resistant depression.

The treatment with antipsychotic drugs, such as olanzapine, may lead to serious side effects. The Food and Drug Administration requires all atypical antipsychotics to include a warning about the risk of developing hyperglycemia and diabetes, both of which are factors in the metabolic syndrome. These effects may be related to the drug's ability to induce weight gain. Cardiometabolic adverse effects, such as weight gain, obesity, hypertension and lipid and glucose abnormalities, are particularly problematic during development because they predict adult obesity, the metabolic syndrome, cardiovascular morbidity and malignancy, especially if used in children and adolescents.

There may be an increased risk of increased blood sugar levels and diabetes with olanzapine as well as the other antipsychotic medications in its class.

Many paediatric and adolescent patients who received second-generation antipsychotic medications experienced significant weight gain, along with varied adverse effects on cholesterol and triglyceride levels and other metabolic measures, according to a study in the October 28 issue of JAMA (JAMA, 2009 Oct. 28, 302 (16), 1765-73).

"Increasingly, the cardiometabolic effects of second-generation antipsychotic medications have raised concern. Cardiometabolic adverse effects, such as age-inappropriate weight gain, obesity, hypertension, and lipid and glucose abnormalities, are particularly problematic during development because they predict adult obesity, the metabolic syndrome, cardiovascular morbidity, and malignancy," the authors wrote. The cardiometabolic effects of these medications have not been sufficiently studied in children and adolescent patients who have not previously received them, according to background information in the article.

Christoph U. Correll, MD, Zucker Hillside Hospital, North Shore-Long Island Jewish Health System, Glen Oaks, and The Feinstein Institute for Medical Research, Manhasset, N.Y., and colleagues conducted a study of weight and metabolic changes in a group of 272 paediatric patients (ages 4 to 19 years) who had not previously received antipsychotic medication. Patients had mood spectrum (47.8%), schizophrenia spectrum (30.1%), and disruptive or aggressive behaviour spectrum (22.1%) disorders. Fifteen patients who refused participation or were nonadherent to medications served as a comparison group. Patients were treated with the antipsychotic medications aripiprazole, olanzapine, quetiapine, or risperidone for 12 weeks.

After a median of 10.8 weeks of treatment, weight increased by an average of 8.5 kg (18.7 lbs) with olanzapine (n=45), by 6.1 kg (13.4 lbs) with quetiapine (n=36), by 5.3 kg (11.7 lbs) with risperidone (n=135), and by 4.4 kg (9.7 lbs) with aripiprazole (n=41) compared with minimal weight change of 0.2 kg (0.4 lbs) in the untreated comparison group (n=15). "Each antipsychotic medication was associated with significantly increased fat mass and waist circumference," the authors wrote. "Altogether, 10% to 36% of patients transitioned to overweight or obese status within 11 weeks."

The researchers also found that adverse changes during the study period reached statistical significance for olanzapine and quetiapine for total cholesterol, triglycerides, non-high-density lipoprotein (HDL) cholesterol, and ratio of triglycerides to HDL cholesterol. "With risperidone, levels of triglycerides increased significantly. Metabolic baseline-to-endpoint changes were not significant with aripiprazole or in the untreated comparison group. Patients receiving quetiapine had modestly higher incidence rates of hyperglycaemia and the metabolic syndrome and patients receiving olanzapine experienced the highest incidence rates."

The authors noted that these results are concerning because they include fat mass and waist circumference, which are associated with the metabolic syndrome in adults treated with antipsychotic medications and heart disease in the general population. "Moreover, abnormal childhood weight and metabolic status adversely affect adult cardiovascular outcomes via continuation of these risk factors or independent or accelerated mechanisms."

"Our results, together with data from first-episode studies, suggest that guidelines for antipsychotic medication exposure for vulnerable paediatric and adolescent patients naïve to antipsychotic medication should consider more frequent [eg, biannual] cardiometabolic monitoring after the first 3 months of treatment. Finally, in view of poor physical health outcomes and suboptimal metabolic monitoring in the severely mentally ill, the benefits of second-generation antipsychotic medications must be balanced against their cardiometabolic risks through a careful assessment of the indications for their use, consideration of lower-risk alternatives, and proactive adverse effect monitoring and management," the authors concluded.

In an accompanying editorial, Christopher K. Varley, MD, and Jon McClellan, MD, of Seattle Children's Hospital, Seattle, Wash., wrote that these findings indicate there are other factors to consider regarding the use of atypical antipsychotic medications in children and adolescents.

"These medications can be lifesaving for youth with serious psychiatric illnesses such as schizophrenia, classically defined bipolar disorder, or severe aggression associated with autism. However, given the risk for weight gain and long-term risk for cardiovascular and metabolic problems, the widespread and increasing use of atypical antipsychotic medications in children and adolescents should be reconsidered."

There is a need for new therapies with improved safety and tolerability profile over current atypical antipsychotics. For example, new treatments should not be associated with such side effects or adverse reactions as described above.

Metabolic syndrome is a combination of medical disorders that increase the risk of developing diabetes and cardiovascular disease. Risk factors include for example abdominal obesity (excessive fat tissue in and around the abdomen), blood fat disorders, elevated blood pressure, insulin resistance or glucose intolerance.

Trace amines (p-tyramine, β-phenylethylamine (PEA), octopamine, and tryptamine) are present throughout the CNS, closely paralleling the monoaminergic pathways, and at endogenous levels much lower than these neurotransmitters. Their scarcity is due, in part, to their high turnover rate being good substrates for MAO A/B. Trace amines are structurally related to, co-localized, and released with classical biogenic amine neurotransmitters. They are suggested to be neuromodulators of classical neurotransmitters like dopamine, serotonin and noradrenaline whose levels are the target of all known antidepressants and most antipsychotics currently on the market or in clinics. Abnormalities in trace amine physiology have long been associated with schizophrenia and mood disorders. In schizophrenia, increased urinary levels of PEA (the so-called endogenous amphetamine), and alterations in the metabolism of tryptamine and p-tyramine have been proposed, including enzymes involved in the synthetic and catabolic pathways of these molecules.

Therefore, the identification of specific receptors for trace amines could lead to the development of specific drugs targeting this novel neuromodulator system with clinical applications in disorders such as schizophrenia, bipolar disorder and depression.

Recently, a family of G-protein coupled receptors has been identified and named Trace Amine-Associated Receptors (TAAR), TAAR1 being the best characterized of these receptors, and the main target for endogenous trace amines. TAAR1 is expressed in brain structures associated with psychiatric disorders, in particular in key areas where modulation of dopamine (ventral tegmental area) and serotonin (dorsal raphe) occurs but also in the amygdala, hypothalamus, nucleus accumbens, rhinal cortices, and subiculum. TAAR1 may be a novel target for antipsychotic drugs with high potential for differentiation, exploring a fundamentally new mechanism of action based on the modulation of dopaminergic and glutamatergic neurotransmission. Therefore, even in the absence of trace amine deficiencies, neuromodulatory effects on the monoaminergic pathways could predictably lead to an improvement in schizophrenia. Also, the TAAR genes map closely to one of the major genetic susceptibility locus for schizophrenia, SCZD5.

LITERATURE

1. Davis B A, Boulton A A (1994) The trace amines and their acidic metabolites in depression—an overview. Prog Neuropsychopharmacol Biol Psychiatry 18, 17-45.
2. Sabelli H, Fink P, Fawcett J, Tom C (1996) Sustained antidepressant effect of PEA replacement. J Neuropsychiatry Clin Neurosci 8, 168-171.
3. Borowsky B, Adham N, Jones K A, Raddatz R, Artymyshyn R, Ogozalek K L, Durkin M M, Lakhlani P P, Bonini J A, Pathirana S, Boyle N, Pu X, Kouranova E, Lichtblau H, Ochoa F Y, Branchek T A, Gerald C (2001) Trace amines: identification of a family of mammalian G protein-coupled receptors. Proc Nat Acad Sci USA 98, 8966-8971.
4. Bunzow J R, Sonders M S, Arttamangkul S, Harrison L M, Zhang G, Quigley D I, Darland T, Suchland K L, Pasumamula S, Kennedy J L, Olson S B, Magenis R E, Amara S G, Grandy D K (2001) Amphetamine, 3,4-methylenedioxymethamphetamine, lysergic acid diethylamide, and metabolites of the catecholamine neurotransmitters are agonists of a rat trace amine receptor. Mol Pharmacol 60, 1181-1188.
5. Branchek T A, Blackburn T P (2003) Trace amine receptors as targets for novel therapeutics: legend, myth and fact. Curr Opin Pharmacol 3, 90-97.
6. Lindemann L, Ebeling M, Kratochwil N A, Bunzow J R, Grandy D K, Hoener M C (2005) Trace amine-associated receptors form structurally and functionally distinct subfamilies of novel G protein-coupled receptors. Genomics 85, 372-385.
7. Lindemann L, Hoener M C (2005) A renaissance in trace amines inspired by a novel GPCR family. Trends Pharmacol Sci 26, 274-281.
8. Burchett S A, Hicks T P (2006) The mysterious trace amines: protean neuromodulators of synaptic transmission in mammalian brain. Prog Neurobiol 79, 223-246.
9. Berry M D (2007) The potential of trace amines and their receptors for treating neurological and psychiatric diseases. Rev Recent Clin Trials 2, 3-19.
10. Wolinsky T D, Swanson C J, Smith K E, Zhong H, Borowsky B, Seeman P, Branchek T, Gerald C P (2007) The trace amine 1 receptor knockout mouse: an animal model with relevance to schizophrenia. Genes Brain Behav 6, 628-639.
11. Lindemann L, Meyer C A, Jeanneau K, Bradaia A, Ozmen L, Bluethmann H, Bettler B, Wettstein J G, Borroni E, Moreau J L, Hoener M C (2008) Trace amine-associated receptor 1 modulates dopaminergic activity. J Pharmacol Exp Ther 324, 948-956.
12. Xie Z, Miller G M (2009) Trace amine-associated receptor 1 as a monoaminergic modulator in brain. Biochem Pharmacol 78, 1095-1104.
13. Sotnikova T D, Caron M G, Gainetdinov R R (2009) Trace amine-associated receptors as emerging therapeutic targets. Mol Pharmacol 76, 229-235.
14. Bradaia A, Trube G, Stalder H, Norcross R D, Ozmen L, Wettstein J G, Pinard A, Buchy D, Gassmann M, Hoener M C, Bettler B (2009) The selective antagonist EPPTB reveals TAAR1-mediated regulatory mechanisms in dopaminergic neurons of the mesolimbic system. Proc Natl Acad Sci USA 106, 20081-20086.

SUMMARY OF THE INVENTION

The present invention provides a pharmaceutical combination for the treatment of schizophrenia and acute manic episodes associated with bipolar disorders, which comprises a compound that is active on a trace amine-associated receptor 1 (TAAR1 agonist) and an antipsychotic drug. Such a combination can reduce metabolic side effects which appear when using an antipsychotic drug alone.

A combination of an antipsychotic drug with a trace amine-associated receptor 1 agonist has the potential to reduce the incidence of metabolic syndrome and positive symptoms in schizophrenia as well as acute manic episodes associated with bipolar disorders.

Based on the above, TAAR1 agonists should be effective agents in the treatment of psychiatric disorders, both directly as well as indirectly by influencing monoaminergic pathways. TAAR1 agonists that have been extensively profiled in non-clinical experiments indicative of antipsychotic, procognitive, antidepressant, and anti-addictive activity, leading to the thought that it may constitute a completely new class of drugs for the treatment of schizophrenia and mood disorders. Based on this profile, TAAR1 agonists may have the potential to treat schizophrenic patients with better efficacy, including ameliorating negative and cognitive symptoms which are not currently treatable with existing therapies, and possibly reducing substance abuse in these patients. Finally, given its beneficial metabolic, anti-diabetic effects, these drugs could provide significant benefits for schizophrenic patients, allowing the control of positive symptoms without increasing metabolic syndrome.

DETAILED DESCRIPTION OF THE INVENTION

Figure 1A:
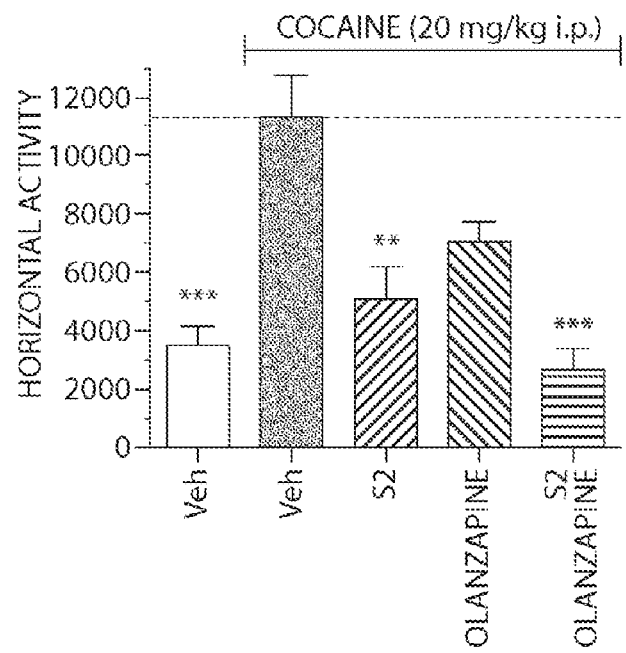
FIG. 1 illustrates the effects on cocaine-induced locomotion in mice.

From the group of TAAR1 agonists compounds have been selected, which are described in WO08/092,785, WO08/098,857, WO2010/010014 and PCT/EP2010/070045 and are of the following structures:

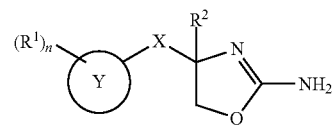

I wherein $R^1$ is hydrogen, deuterium, tritium, $C_{1-7}$-alkyl, hydroxy, $C_{1-7}$-alkoxy, $C_{1-7}$-alkyl substituted by halogen, $C_{1-7}$-alkoxy substituted by halogen, halogen, phenyl optionally substituted by halogen, or is phenyloxy, benzyl, benzyloxy, —COO—$C_{1-7}$-alkyl, —O—$(CH_2)_o$—O—$C_{1-7}$-alkyl, NH-cycloalkyl, cycloalkyl or tetrahydropyran-4-yloxy, wherein the substituents for n>1 are the same or different;

X is a bond, —CHR—, —CHRCHR'—, —OCH$_2$—, —NRCHR', —OCHRCHR', —CH$_2$OCHR—, —CH$_2$CH$_2$CH$_2$—, —SCH$_2$—, —S(O)$_2$CH$_2$—, —CH$_2$SCH$_2$—, —CH$_2$N(R)CH$_2$—, -cycloalkyl-CH$_2$— or SiRR'—CH$_2$—;

R and R' are each independently hydrogen, $C_{1-7}$-alkyl or $C_{1-7}$-alkyl substituted by halogen;

$R^2$ is hydrogen, phenyl or $C_{1-7}$-alkyl;

Y is phenyl, naphthyl, thiophenyl, pyridinyl, cycloalkyl, 1,2,3,4-tetrahydro-naphthalen-2-yl, 2,3-dihydrobenzo[1,4]dioxin-6-yl or benzo[1,3]dioxol-5-yl;

n is 0, 1, 2 or 3;

o is 2 or 3;

or a pharmaceutically suitable acid addition salt.

More specifically, the TAAR1 receptor agonists are of the following structure

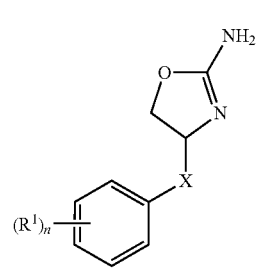

I-1 wherein $R^1$ is hydrogen, $C_{1-7}$-alkyl, hydroxy, $C_{1-7}$-alkoxy, $C_{1-7}$-alkyl substituted by halogen, $C_{1-7}$-alkoxy substituted by halogen or halogen, wherein the substituents for n=2 are the same or different;

X is a bond, —NRCHR', —CHRCHR' or —OCHRCHR';

R and R' are each independently hydrogen, $C_{1-7}$-alkyl;

n is 1 or 2;

or are compounds of formula

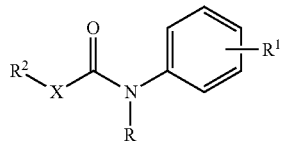

wherein
R is hydrogen or $C_{1-7}$-alkyl;
$R^1$ is —$(CH_2)_n$—$(O)_o$-heterocycloalkyl, optionally substituted by $C_{1-7}$-alkyl, hydroxy, halogen, or by —$(CH_2)_p$-aryl;
n is 0, 1 or 2;
o is 0 or 1;
p is 0, 1 or 2;
$R^2$ is cycloalkyl, heterocycloalkyl, or is aryl or heteroaryl, wherein the aromatic rings are optionally substituted by one or two substituents, selected from $C_{1-7}$-alkyl, halogen, heteroaryl, $CF_3$, $OCF_3$, $OCH_2CF_3$, $C_{1-7}$-alkoxy, $CH_2$—$C_{1-7}$-alkoxy, $C_{2-7}$-alkynyl or cyano;
X is a bond, —NR'—, —$CH_2NH$—, —CHR''—, —$(CH_2)_q$—O— or —$(CH_2)_2$—;
R' is hydrogen or $C_{1-7}$-alkyl,
R'' is hydrogen, $C_{1-7}$-alkyl, $C_{1-7}$-alkoxy,
q is 0, 1 or 2;
or a pharmaceutically suitable acid addition salt thereof.
or are more specifically compounds of formula II-1

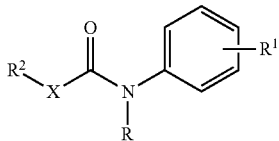

wherein
R is hydrogen;
$R^1$ is pyrrolidinyl;
$R^2$ is aryl or heteroaryl, wherein the aromatic rings are optionally substituted by halogen;
X is a bond or —NR'—;
R' is hydrogen or $C_{1-7}$-alkyl,
or a pharmaceutically suitable acid addition salt thereof.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, or tert-butyl. The term "$C_{1-7}$-alkyl" denotes and alkyl group having from 1 to 7 carbon atoms.

As used herein, the term "$C_{1-7}$-alkoxy" denotes a group wherein the alkyl residue is as defined above and which is attached via an oxygen atom.

As used herein, the term "$C_{1-7}$-alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

The term "halogen" denotes chlorine, iodine, fluorine and bromine.

The term "cycloalkyl" denotes an alkylene ring, containing from 3 to 6 carbon ring atoms.

The term "alkynyl" denotes a straight-chain or branched hydrocarbon residue comprising a triple bond and up to 7, preferably up to 4 carbon atoms, such as e.g. ethynyl or 2-propynyl.

The term "aryl", denotes an aromatic carbon ring system having 6 to 12 ring atoms, such as phenyl or naphthyl, preferably phenyl.

The term "heteroaryl" refers to an aromatic 5 to 6 membered monocyclic ring or 9 to 10 membered bicyclic ring which contains 1, 2 or 3 heteroatoms selected from nitrogen, oxygen and/or sulphur, for example, pyridinyl, pyrazolyl, pyrimidinyl, benzoimidazolyl, quinolinyl and isoquinolinyl.

The term "heterocycloalkyl" denotes a non-aromatic 5 to 6 membered monocyclic ring which contains 1, 2 or 3 heteroatoms selected from nitrogen, oxygen and/or sulphur, for example piperazinyl, piperidinyl, morpholinyl, pyrrolidinyl and thiomorpholinyl.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgement of the attending medical or veterinary practitioner, and other factors.

Specific compounds, which have been used in the examples as described below, are the followings:
S1=(S)-4-(S)-2-phenyl-butyl)-4,5-dihydro-oxazol-2-ylamine;
S2=(S)-4-(3-fluoro-2-methyl-phenyl)-4,5-dihydro-oxazol-2-ylamine;
S3=(S)-4-(4-chloro-2-trifluoromethyl-phenyl)-4,5-dihydro-oxazol-2-ylamine;
S4=(S)-4-[(ethyl-phenyl-amino)-methyl]-4,5-dihydro-oxazol-2-ylamine;
S5=3-[(S)-1-((S)-2-amino-4,5-dihydro-oxazol-4-ylmethyl)-propoxy]-phenol;
S6=5-chloro-pyridine-2-carboxylic acid (4-pyrrolidin-3-yl-phenyl)-amide;
S7=4-chloro-N-(4-pyrrolidin-3-yl-phenyl)-benzamide;
S8=1-(5-chloro-pyridin-2-yl)-3-(4-pyrrolidin-3-yl-phenyl) urea;
S9=(S)-4-[(S)-1-(4-fluoro-phenyl)-ethoxymethyl]-4,5-dihydro-oxazol-2-ylamine;
S10=5-chloro-pyrimidine-2-carboxylic acid {4-[2-((S)-2-amino-4,5-dihydro-oxazol-4-yl)-ethyl]-phenyl}-amide;
S11=N-{4-[2-((S)-2-amino-4,5-dihydro-oxazol-4-yl)-ethyl]-phenyl}-4-chloro-benzamide;

S12=(R)-2-chloro-6-methyl-N-(4-(morpholin-2-yl)phenyl)isonicotinamide;
S13=(S)—N-(4-(morpholin-2-yl)phenyl)-6-(2,2,2-trifluoroethoxy)nicotinamide;
S14=(S)—N-(4-(morpholin-2-yl)phenyl)-2-(trifluoromethyl)isonicotinamide;
S15=(S)-1-(4-fluorobenzyl)-3-(4-(morpholin-2-yl)phenyl)urea;
S16=(S)-1-(3-cyanophenyl)-3-(4-(morpholin-2-yl)phenyl)urea; and
S17=(S)-6-chloro-N-(4-(morpholin-2-yl)phenyl)nicotinamide.

The specific combination of an antipsychotic drug, especially olanzapine, and a TAAR1 agonist as mentioned above may reduce some undesired metabolic side effects.

In one embodiment, the invention provides the combination of an atypical antipsychotic drug and a TAAR1 agonist, wherein the preferred atypical antipsychotic drug is olanzapine and the preferred TAAR1 agonist is a compound of formulas I, I-1, II or II-1. More specifically, the TAAR1 agonist is a compound selected from S1 to S17.

In another embodiment, the invention provides the novel compound S2, which is (S)-4-(3-fluoro-2-methyl-phenyl)-4,5-dihydro-oxazol-2-ylamine, encompassed by formulas I or I-1. In still another embodiment, the invention provides the combination comprising olanzapine and a TAAR1 agonist for the treatment of schizophrenia and manic episodes associated with bipolar disorders with reduced incidence of metabolic syndrome, wherein the reduced incidence of metabolic syndrome results from antidiabetic efficacy with lowering blood glucose excursion, fat mass and body weight.

In yet another embodiment, the invention provides the use of a combination comprising olanzapine and a TAAR1 agonist for the treatment of schizophrenia and manic episodes associated with bipolar disorders with reduced incidence of metabolic syndrome, wherein the reduced incidence of metabolic syndrome results from antidiabetic efficacy with lowering blood glucose excursion, fat mass and body weight.

In another embodiment, the invention provides the use of a combination comprising olanzapine and a TAAR1 agonist for the manufacture of a medicament for the treatment of schizophrenia and manic episodes associated with bipolar disorders with reduced incidence of metabolic syndrome, wherein the reduced incidence of metabolic syndrome results from antidiabetic efficacy with lowering blood glucose excursion, fat mass and body weight.

In one embodiment, the present invention provides a method for the treatment of schizophrenia and manic episodes associated with bipolar disorders with reduced incidence of metabolic syndrome, wherein the reduced incidence of metabolic syndrome results from antidiabetic efficacy with lowering blood glucose excursion, fat mass and waist comprising administering to a human in need thereof an effective amount of a combination comprising an atypical antipsychotic drug and a TAAR1 agonist.

In another embodiment, the present invention provides a method for the treatment of schizophrenia and manic episodes associated with bipolar disorders with reduced incidence of metabolic syndrome, wherein the reduced incidence of metabolic syndrome results from antidiabetic efficacy with lowering blood glucose excursion, fat mass and waist, wherein the atypical antipsychotic drug is olanzapine and the TAAR1 agonists are as described in formulas I, I-1, II and II-1.

In still another embodiment, the present invention provides a pharmaceutical composition comprising a combination of an atypical antipsychotic drug and a TAAR1 agonist as described in formulas I, I-1, II and II-1, together with pharmaceutically acceptable excipients for the treatment of schizophrenia and manic episodes associated with bipolar disorders with reduced incidence of metabolic syndrome, wherein the reduced incidence of metabolic syndrome results from antidiabetic efficacy with lowering blood glucose excursion, fat mass and body weight.

The TAAR1 agonists can be prepared as follows:

Example S1

(S)-4-((S)-2-Phenyl-butyl)-4,5-dihydro-oxazol-2-ylamine

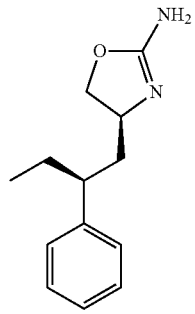 [SMILES: CC[C@@H](C[C@H]1COC(N)=N1)c1ccccc1]

a) (R)-1-Iodomethyl-propyl)-benzene

To a solution of triphenylphosphine (15.4 g, 59 mmol) and imidazole (3.99 g, 59 mmol) in dichloromethane (150 ml) at room temperature was added portionwise iodine (14.9 g, 50 mmol) at such a rate that the temperature of the reaction mixture did not rise above 30° C. To the mixture was then added a solution of (R)-2-phenyl-butan-1-ol (7.34 g, 41 mmol, CAS 16460-75-6) in dichloromethane (50 ml) and the mixture was then stirred at room temperature overnight. The mixture was then concentrated in vacuo and the residue was resuspended in ether and the resulting crystals collected by filtration. The filtrate was concentrated in vacuo and the residue was triturated in heptane. The resulting crystals were removed by filtration and the filtrate was concentrated in vacuo. The residue was purified by column chromatography ($SiO_2$, heptane/EtOAc) to yield a colourless oil, (6.38 g, 60%).

b) (2R,5S)-2-Isopropyl-3,6-dimethoxy-5-((S)-2-phenyl-butyl)-2,5-dihydro-pyrazine A solution of (2R)-(−)-2,5-dihydro-3,6-dimethoxy-2-isopropylpyrazine (4.25 g, 23.1 mmol) in tetrahydrofuran (30 ml) was cooled to −78° C., then n-butyllithium (1.6 M in hexane, 15.1 ml, 24.2 mmol) was added and the mixture was stirred for 1 hour. A solution of ((R)-1-iodomethyl-propyl)-benzene (6.30 g, 24.2 mmol) in tetrahydrofuran (30 ml) was added dropwise over 30 min and the mixture was stirred overnight while being allowed to warm slowly from −70° C. to room temperature. The reaction was quenched by addition of saturated aqueous ammonium chloride solution and the mixture was extracted with ether. The organic layer was separated, washed with saturated brine, then dried over $Na_2SO_4$ and concentrated in vacuo. The residue was purified by column chromatography ($SiO_2$, heptane/EtOAc) to yield a light yellow oil (4.69 g, 64%); MS (ISP): 317.0 ([M+H]$^+$).

c) (2S,4S)-2-Amino-4-phenyl-hexanoic acid methyl ester

To a solution of trifluoroacetic acid (3.4 ml) in water (440 ml) was added dropwise over 15 min a solution of (2R,5S)-

2-isopropyl-3,6-dimethoxy-5-((S)-2-phenyl-butyl)-2,5-dihydro-pyrazine (4.69 g, 14.8 mmol) in acetonitrile (75 ml). The mixture was stirred overnight at room temperature made basic by addition of saturated aqueous sodium carbonate solution and the mixture was extracted with ethyl acetate. The phases were separated and the organic phase was washed sequentially with water and with saturated brine, then dried over Na$_2$SO$_4$, filtered and concentrated in vacuo. The residue was purified by column chromatography (SiO$_2$, EtOAc/heptane) to yield a yellow oil (2.78 g, 85%); MS (ISP): 222.1 ([M+H]$^+$).

d) (2S,4S)-2-Amino-4-phenyl-hexan-1-ol

To a suspension of lithium aluminum hydride (121 mg, 3.18 mmol) in tetrahydrofuran (8 ml) was added a solution of (2S,4S)-2-amino-4-phenyl-hexanoic acid methyl ester (320 mg, 1.45 mmol) in tetrahydrofuran (10 ml) and the mixture was stirred for 16 hours. The reaction was quenched by dropwise addition of ethyl acetate, then acidified to pH 5 by addition of hydrochloric acid and then made basic by addition of saturated aqueous sodium bicarbonate solution. The mixture was taken up in ethyl acetate/tetrahydrofuran (1:1), the phases were separated and the organic phase was washed sequentially with water and with saturated brine. The organic phase was then dried over Na$_2$SO$_4$ and concentrated in vacuo. The residue was purified by chromatography (column: Isolute® Flash-NH$_2$ from Separtis; eluent: dichloromethane/MeOH) to yield a yellow oil, (116 mg, 42%); MS (ISP): 194.4 ([M+H]$^+$).

e) (S)-4-(S)-2-Phenyl-butyl)-4,5-dihydro-oxazol-2-ylamine

To a stirred, cooled (0° C.) solution of (2S,4S)-2-amino-4-phenyl-hexan-1-ol (270 mg, 1.40 mmol) and sodium acetate (229 mg, 2.70 mmol) in methanol (20 ml) was added dropwise a solution of cyanogen bromide (180 mg, 1.68 mmol) in methanol (2 ml) over 10 min. The mixture was then allowed to warm to r.t. and stirring was continued for 16 h. The mixture was concentrated in vacuo and the residue was taken up in ethyl acetate and washed sequentially with saturated aqueous sodium bicarbonate solution and with saturated brine. The organic phase was dried over sodium sulphate and concentrated in vacuo. The residue was purified by chromatography (column: Isolute® Flash-NH$_2$ from Separtis; eluent: heptane/EtOAc/MeOH) to yield a light yellow solid. MS (ISP): 219.3 ([M+H]$^+$).

S2

(S)-4-(3-fluoro-2-methyl-phenyl)-4,5-dihydro-oxazol-2-ylamine

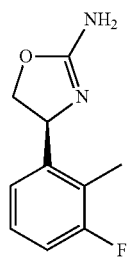

a) (RS)-Amino-(3-fluoro-2-methyl-phenyl)-acetonitrile

To a stirred solution of 3-fluoro-2-methyl-benzaldehyde (5.0 g) in methanol (20 ml) were added sequentially ammonia solution (40.5 ml, 7 M solution in methanol) and tetraisopropyl orthotitanate (12.6 ml) and the resulting mixture was stirred at r.t. for 1 h. Trimethylsilylcyanide (4.69 ml) was then added dropwise and stirring continued at r.t. overnight. The reaction mixture was poured onto ice-water (400 ml) and the mixture was then extracted twice with ethyl acetate. The combined organic phases were washed with brine and then dried over sodium sulphate and concentrated in vacuo to afford (RS)-amino-(3-fluoro-2-methyl-phenyl)-acetonitrile (5.90 g, quant.) as an orange solid. $^1$H NMR δ (CDCl$_3$, 300 MHz): 7.39 (1H, d, J=7.3 Hz), 7.31 (1H, m), 7.17 (1H, dd, J=9.6 & 9.6 Hz), 5.16 (1H, t, J=7.8 Hz), 5.16 (1H, d, J=7.8 Hz), 2.26 (1H, d, J=2.1 Hz).

b) (RS)-Amino-(3-fluoro-2-methyl-phenyl)-acetic acid (RS)-Amino-(3-fluoro-2-methyl-phenyl)-acetonitrile (5.89 g) was suspended in 5 N aq hydrochloric acid (40 ml) and the mixture was heated at reflux for 18 h. The mixture was then extracted with ethyl acetate and the aqueous phase was concentrated in vacuo. The residue was resuspended in isopropanol and concentrated in vacuo again. The residue was taken up in water and neutralised by dropwise addition of 1 N aq NaOH, whereby white crystals slowly formed. The crystals were collected by filtration and dried in vacuo at 50° C. to afford (RS)-amino-(3-fluoro-2-methyl-phenyl)-acetic acid (7.1 g, quant.) as an off-white solid. MS (ISP): 184.1 ([M+H]$^+$).

c) (RS)-2-Amino-2-(3-fluoro-2-methyl-phenyl)-ethanol

To a stirred solution of lithium borohydride in THF (48.9 ml, 2 M solution) under an argon atmosphere was added dropwise chlorotrimethylsilane (25.0 ml). The resulting suspension was cooled to 0° C. and (RS)-amino-(3-fluoro-2-methyl-phenyl)-acetic acid (7.1 g) was added portionwise, whereby the temperature of the reaction mixture rose transiently to 45° C. The ice bath was removed and stirring was then continued at r.t. for 90 min. The mixture was quenched by dropwise addition of methanol (20 ml) and then concentrated in vacuo. The residue was suspended in ethyl acetate and washed with 2 N aq NaOH. The phases were separated and the aqueous phase was extracted with ethyl acetate. The combined organic phases were dried over sodium sulphate and concentrated in vacuo to afford (RS)-2-amino-2-(3-fluoro-2-methyl-phenyl)-ethanol (1.83 g, 28%) as a light yellow solid. MS (ISP): 170.3 ([M+H]$^+$).

d) (RS)-4-(3-Fluoro-2-methyl-phenyl)-4,5-dihydro-oxazol-2-ylamine

To a stirred, cooled (0° C.) solution of (RS)-2-amino-2-(3-fluoro-2-methyl-phenyl)-ethanol (1.82 g) and sodium acetate (1.72 g) in methanol (17 ml) was added dropwise a solution of cyanogen bromide (1.18 g) in methanol (8 ml) over 10 min. The mixture was then stirred for 1 h at 0° C., then was allowed to warm to at r.t. and stirring continued for 2 h. The mixture was concentrated in vacuo and the residue was resuspended in water and made basic by addition of 1 M aq sodium hydroxide solution. The mixture was then extracted twice with dichloromethane and the combined organic phases were dried over sodium sulphate and concentrated in vacuo. The residue was purified by column chromatography (SiO$_2$; gradient: dichloromethane/methanol) to give (RS)-4-(3-fluoro-2-methyl-phenyl)-4,5-dihydro-oxazol-2-ylamine (0.85 g, 41%) as a light yellow solid. MS (ISP): 195.3 ([M+H]$^+$).

e) (+)-(S)-4-(3-Fluoro-2-methyl-phenyl)-4,5-dihydro-oxazol-2-ylamine & (−)-(R)-4-(3-Fluoro-2-methyl-phenyl)-4,5-dihydro-oxazol-2-ylamine (RS)-4-(3-fluoro-2-methyl-phenyl)-4,5-dihydro-oxazol-2-ylamine was separated by chiral HPLC (Chiralpak A D, EtOH/heptane=10:90) to yield (−)-(R)-4-(3-fluoro-2-methyl-phenyl)-4,5-dihydro-oxazol-2-ylamine (white solid; MS (ISP): 195.3 ([M+H]$^+$)) as the first fraction and (+)-(S)-4-(3-fluoro-2-methyl-phenyl)-4,5-dihydro-oxazol-2-ylamine (white solid; MS (ISP): 195.3 ([M+H]$^+$)) as the second fraction.

S3

(+)-(S)-4-(4-Chloro-2-trifluoromethyl-phenyl)-4,5-dihydro-oxazol-2-ylamine

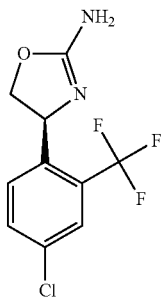 [SMILES: NC1=N[C@@H](c2ccc(Cl)cc2C(F)(F)F)CO1]

a) (RS)-4-(4-Chloro-2-trifluoromethyl-phenyl)-4,5-dihydro-oxazol-2-ylamine

This was prepared in analogy to example S2 (steps a-d) starting from 4-chloro-2-trifluoromethyl-benzaldehyde in place of 3-fluoro-2-methyl-benzaldehyde. White solid. MS (ISP): 267.1 ([{$^{37}$Cl}M+H]$^+$), 265.0 ([{$^{35}$Cl}M+H]$^+$).

b) (+)-(S)-4-(4-Chloro-2-trifluoromethyl-phenyl)-4,5-dihydro-oxazol-2-ylamine & (−)-(R)-4-(4-Chloro-2-trifluoromethyl-phenyl)-4,5-dihydro-oxazol-2-ylamine (RS)-4-(4-Chloro-2-trifluoromethyl-phenyl)-4,5-dihydro-oxazol-2-ylamine was separated by chiral HPLC (Chiralpak A D, EtOH/heptane=5:95) to yield (+)-(S)-4-(4-chloro-2-trifluoromethyl-phenyl)-4,5-dihydro-oxazol-2-ylamine (white solid; MS (ISP): 267.1 ([{$^{37}$Cl}M+H]$^+$), 265.0 ([{$^{35}$Cl}M+H]$^+$)) as the first fraction and (−)-(R)-4-(4-chloro-2-trifluoromethyl-phenyl)-4,5-dihydro-oxazol-2-ylamine (white solid; MS (ISP): 267.1 ([{$^{37}$Cl}M+H]$^+$), 265.0 ([{$^{35}$Cl}M+H]$^+$)) as the second fraction.

S4

(S)-4-[(Ethyl-phenyl-amino)-methyl]-4,5-dihydro-oxazol-2-ylamine

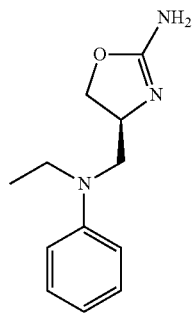 [SMILES: CCN(C[C@H]1COC(N)=N1)c1ccccc1]

a) (S)-4-[(Ethyl-phenyl-amino)-methyl]-2,2-dimethyl-oxazolidine-3-carboxylic acid tert-butyl ester To a stirred solution of tert-butyl (R)-(+)-4-formyl-2,2-dimethyl-3-oxazolinecarboxylate (681 mg, CAS 95715-87-0) at r.t. in 1,2-dichloroethane (10 ml) under an argon atmosphere were added molecular sieves 4 Å (1.5 g) and N-ethylaniline (0.25 ml). After stirring for 15 min at r.t., sodium triacetoxyborohydride (1.68 g) was added in one portion, followed by acetic acid (5 drops) and stirring at r.t. was continued overnight. The mixture was quenched by the careful addition of 10% KHCO$_3$ (15 ml). The biphasic mixture was stirred at r.t. for 20 min and filtered. The aqueous phase of the filtrate was back extracted with CH$_2$Cl$_2$. The combined organics were washed with H$_2$O and brine, dried over MgSO$_4$, filtered and concentrated in vacuo. The crude product was purified by column chromatography (SiO$_2$; gradient: cyclohexane→cyclohexane/EtOAc 4:1) to give (S)-4-[(ethyl-phenyl-amino)-methyl]-2,2-dimethyl-oxazolidine-3-carboxylic acid tert-butyl ester (469 mg, 57%) as an orange viscous oil. MS (ISP): 335.5 ([M+H]$^+$).

b) (S)-2-Amino-3-(ethyl-phenyl-amino)-propan-1-ol

To a stirred solution of (S)-4-[(ethyl-phenyl-amino)-methyl]-2,2-dimethyl-oxazolidine-3-carboxylic acid tert-butyl ester (462 mg) at r.t. in dioxane (5.85 ml) under an argon atmosphere was added HCl solution (4 M in dioxane; 4.14 ml). The mixture was stirred at r.t. overnight and concentrated. The residue was taken up in EtOAc and washed with 10% aq. potassium bicarbonate solution. The aqueous layer was back extracted with EtOAc. The combined organics were washed with water and then with brine, dried over MgSO$_4$ and concentrated in vacuo. The crude product was purified by column chromatography (Isolute® SPE flash NH2 column, aminopropyl-functionalized silica; CH$_2$Cl$_2$/MeOH 9:1) to give (S)-2-amino-3-(ethyl-phenyl-amino)-propan-1-ol (133 mg, 62%) as a light brown viscous oil. MS (ISP): 195.1 ([M+H]$^+$).

c) (S)-4-[(Ethyl-phenyl-amino)-methyl]-4,5-dihydro-oxazol-2-ylamine

To a stirred solution of (S)-2-amino-3-(ethyl-phenyl-amino)-propan-1-ol (128 mg) at r.t. in THF (5 ml) under an argon atmosphere were added potassium carbonate (182 mg) and a solution of cyanogen bromide (140 mg) in THF (5 ml). Stirring at r.t. was continued for 21 h. The mixture (off-white suspension) was diluted with EtOAc and washed with H₂O. The aqueous phase was back extracted with EtOAc. The combined organics were washed with brine, dried over MgSO₄, filtered and concentrated in vacuo. The crude product was purified by column chromatography (Isolute® SPE flash NH2 column, aminopropyl-functionalized silica; gradient: CH₂Cl₂→CH₂Cl₂/MeOH 9:1) to provide (S)-4-[(ethyl-phenyl-amino)-methyl]-4,5-dihydro-oxazol-2-ylamine (108 mg, 75%) as an off-white solid. MS (ISP): 220.4 ([M+H]⁺).

S5

3-[(S)-1-((S)-2-Amino-4,5-dihydro-oxazol-4-ylm-ethyl)-propoxy]-phenol

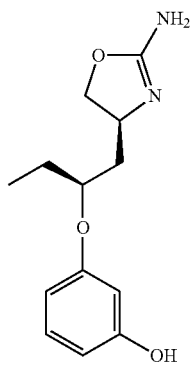 [SMILES: CC[C@@H](C[C@H]1COC(N)=N1)Oc1cccc(O)c1]

a) (S)-4-(R)-2-Hydroxy-butyl)-2,2-dimethyl-oxazoli-dine-3-carboxylic acid tert-butyl ester and (S)-4-(S)-2-Hydroxy-butyl)-2,2-dimethyl-oxazolidine-3-car-boxylic acid tert-butyl ester To a stirred solution of (S)-2,2-dimethyl-4-(2-oxo-ethyl)-oxazolidine-3-carboxylic acid tert-butyl ester (15.5 g; CAS 147959-19-1) in dry diethyl ether (100 ml) under an argon atmosphere at room temperature was added dropwise a solution of ethylmagnesium bromide in diethyl ether (42.6 ml, 3 M solution) and stirring continued for 1 hour. The reaction mixture was then quenched by careful addition of water (10 ml) and the mixture was then filtered through decalite. The filtrate was washed sequentially with water and with saturated brine and then the organic phase was separated, dried over sodium sulphate, filtered and concentrated in vacuo. The reside was purified by column chromatography (SiO₂; gradient: heptane/EtOAc 100:0→50:50) to give (S)-4-(R)-2-hy-droxy-butyl)-2,2-dimethyl-oxazolidine-3-carboxylic acid tert-butyl ester (7.30 g) from fractions eluting first and (S)-4-(S)-2-hydroxy-butyl)-2,2-dimethyl-oxazolidine-3-carboxy-lic acid tert-butyl ester (6.44 g) from fractions eluting later, both compounds as colourless oils. (S)-4-(R)-2-Hydroxy-bu-tyl)-2,2-dimethyl-oxazolidine-3-carboxylic acid tert-butyl ester: ¹H NMR δ (CDCl₃, 300 MHz): 4.52 (1H, br. D, J=3.3 Hz), 4.23 (1H, m), 4.00 (1H, dd, J=8.7 & 5.4 Hz), 3.66 (1H, d, J=8.7 Hz), 3.40 (1H, m), 1.79 (1H, td, J=11.4 & 2.1 Hz), 1.60-1.44 (16H, m), 0.95 (3H, t, J=7.5 Hz). (S)-4-((S)-2-Hydroxy-butyl)-2,2-dimethyl-oxazolidine-3-carboxylic acid tert-butyl ester: ¹H NMR δ (CDCl₃, 300 MHz): 4.12 (1H, m), 3.98 (1H, dd, J=9.0 & 5.7 Hz), 3.82 (1H, m), 3.55 (1H, m), 2.88 (1H, br. s), 1.79 (1H, m), 1.70-1.40 (16H, m), 0.95 (3H, t, J=7.5 Hz).

b) (S)-4-[(S)-2-(3-Benzyloxy-phenoxy)-butyl]-2,2-dimethyl-oxazolidine-3-carboxylic acid tert-butyl ester To a stirred solution of 3-benzyloxy-phenol (264 mg) in THF (5 ml) were added sequentially triphenylphosphine (364 mg) and di-tert-butyl azodicarboxylate (309 mg) and the resulting yellow solution was stirred at room temperature for 15 min. A solution of (S)-4-(R)-2-hydroxy-butyl)-2,2-dim-ethyl-oxazolidine-3-carboxylic acid tert-butyl ester (300 mg) in THF (5 ml) was then added dropwise and the resulting mixture was stirred at 70° C. for 90 min. The reaction mixture was cooled to room temperature and concentrated in vacuo. The crude product was purified by column chromatography (SiO₂; gradient: heptane/EtOAc 100:0→70:30) to give (S)-4-[(S)-2-(3-benzyloxy-phenoxy)-butyl]-2,2-dimethyl-ox-azolidine-3-carboxylic acid tert-butyl ester (1.35 g, 34%) as a colourless viscous oil. MS (ISP): 456.4 ([M+H]⁺).

c) (2S,4S)-2-Amino-4-(3-benzyloxy-phenoxy)-hexan-1-ol

To a solution of trifluoroacetic acid (0.07 ml) in water (6 ml) was added dropwise a solution of (S)-4-[(S)-2-(3-benzy-loxy-phenoxy)-butyl]-2,2-dimethyl-oxazolidine-3-carboxy-lic acid tert-butyl ester (135 mg) in acetonitrile (1 ml). The mixture was heated for 4 h at 80° C. with mechanical shaking. The mixture was then cooled to room temperature and diluted with 1 N aqueous sodium hydroxide solution. The mixture was extracted twice with ethyl acetate and the combined organic phases were dried over sodium sulphate and concentrated in vacuo to give (2S,4S)-2-amino-4-(3-benzyloxy-phe-noxy)-hexan-1-ol (94 mg, quant.) as a light yellow viscous oil. MS (ISP): 316.1 ([M+H]⁺).

d) (S)-4-[(S)-2-(3-Benzyloxy-phenoxy)-butyl]-4,5-dihydro-oxazol-2-ylamine

To a stirred mixture of (2S,4S)-2-amino-4-(3-benzyloxy-phenoxy)-hexan-1-ol (90 mg) and sodium acetate (46 mg) in methanol (2 ml) under an argon atmosphere was added a solution of cyanogen bromide (37 mg) in methanol (1 ml). The mixture was stirred for 18 hours then diluted with 1 N aqueous sodium hydroxide solution. The mixture was extracted twice with dichloromethane and the combined organic phases were dried over sodium sulphate and concentrated in vacuo. The crude product was purified by column chromatography (column: Isolute® Flash-NH₂ from Sepa-rtis; gradient: dichloromethane/MeOH 100:0→95:5) to afford (S)-4-[(S)-2-(3-benzyloxy-phenoxy)-butyl]-4,5-dihy-dro-oxazol-2-ylamine (69 mg, 71%) as a light yellow gum. MS (ISP): 341.1 ([M+H]⁺).

e) 3-[(S)-1-((S)-2-Amino-4,5-dihydro-oxazol-4-ylm-ethyl)-propoxy]-phenol

To a solution of (S)-4-[(S)-2-(3-benzyloxy-phenoxy)-bu-tyl]-4,5-dihydro-oxazol-2-ylamine (60 mg) in methanol (3 ml) at room temperature was added 10% palladium on charcoal (19 mg). The mixture was stirred under an atmosphere of hydrogen (1 atm) at room temperature for 1 h. The catalyst was removed by filtration through decalite, washing with methanol and with dichloromethane, and the filtrate was concentrated in vacuo to yield 3-[(S)-1-(S)-2-amino-4,5-dihydro-oxazol-4-ylmethyl)-propoxy]-phenol as a white solid (44 mg, quant.); MS (ISP): 251.2 ([M+H]$^+$).

S6

(RS)-4-Chloro-N-(4-pyrrolidin-3-yl-phenyl)-benzamide hydrochloride

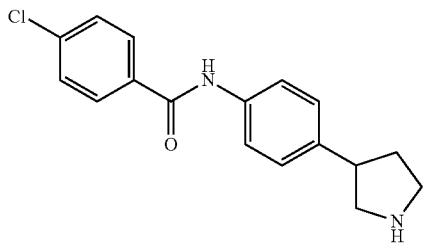 [SMILES: O=C(Nc1ccc(C2CCNC2)cc1)c1ccc(Cl)cc1]

(RS)-3-[4-(4-Chloro-benzoylamino)-phenyl]-pyrrolidine-1-carboxylic acid tert-butyl ester To a stirred suspension of (RS)-tert-butyl 3-(4-aminophenyl)pyrrolidine-1-carboxylate (1.9 g, CAS 908334-28-1) in THF (50 ml) were added sequentially triethylamine (2.0 ml) and 4-chloro-benzoyl chloride (0.93 ml) and stirring was continued at room temperature for 3 h. The mixture was then diluted with ethyl acetate. Water was added and the mixture was acidified to pH 1 by addition of 1 M aq. hydrochloric acid. The organic phase was separated and washed sequentially with aqueous sodium hydroxide solution and with saturated brine. The organic phase was then dried over sodium sulphate and concentrated in vacuo to give (RS)-3-[4-(4-chloro-benzoylamino)-phenyl]-pyrrolidine-1-carboxylic acid tert-butyl ester (2.42 g, 83%) as a white solid which was used in the next step without further purification.

b) (RS)-4-Chloro-N-(4-pyrrolidin-3-yl-phenyl)-benzamide hydrochloride

To a stirred solution of (RS)-3-[4-(4-chloro-benzoylamino)-phenyl]-pyrrolidine-1-carboxylic acid tert-butyl ester (2.36 g) in THF (30 ml) was added dropwise a solution of hydrogen chloride in dioxane (22 ml, 4 M solution) and the mixture was heated at 60° C. overnight. The mixture was then cooled to 0° C. and the ensuing crystals were collected by filtration, washing with diethyl ether, and then dried in vacuo at 60° C. to afford (RS)-4-chloro-N-(4-pyrrolidin-3-yl-phenyl)-benzamide hydrochloride (1.65 g, 83%) as a white crystalline solid. MS (ISP): 303.2 ([{$^{37}$Cl}M+H]$^+$), 301.3 ([{$^{35}$Cl}M+H]$^+$).

S7

(RS)-1-(5-Chloro-pyridin-2-yl)-3-(4-pyrrolidin-3-yl-phenyl)-urea hydrochloride

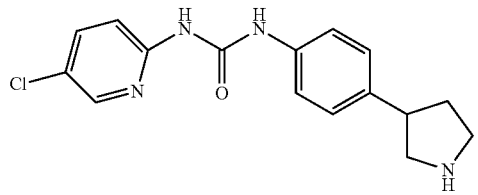 [SMILES: O=C(Nc1ccc(C2CCNC2)cc1)Nc1ccc(Cl)cn1]

a) (RS)-3-{4-[3-(5-Chloro-pyridin-2-yl)-ureido]-phenyl}-pyrrolidine-1-carboxylic acid tert-butyl ester To a stirred suspension of 2-amino-5-chloro-pyridine (1.01 g) in dichloroethane (20 ml) was added portionwise triphosgene (831 mg). Triethylamine (2.22 ml) was then added dropwise and the mixture was stirred at 50° C. for 1 h. The mixture was then concentrated in vacuo to afford a beige solid containing a mixture of triethylammonium chloride and 5-chloro-2-isocyanato-pyridine. This solid was then added to a stirred solution of (RS)-tert-butyl 3-(4-aminophenyl)pyrrolidine-1-carboxylate (350 mg, CAS 908334-28-1) and N,N-diisopropylethylamine (0.68 ml) in dichloroethane (6 ml) and the resulting mixture was stirred at 60° C. overnight. The mixture was then diluted with dichloromethane and washed with water. The phases were separated and the organic phase was dried over sodium sulphate and concentrated in vacuo. The residue was purified by column chromatography (SiO$_2$; gradient: heptane/EtOAc) to give (RS)-3-{4-[3-(5-chloro-pyridin-2-yl)-ureido]-phenyl}-pyrrolidine-1-carboxylic acid tert-butyl ester (212 mg, 38%) as an off-white solid. MS (ISP): 419.2 ([{$^{37}$Cl}M+H]$^+$), 417.2 ([{$^{35}$Cl}M+H]$^+$).

b) (RS)-1-(5-Chloro-pyridin-2-yl)-3-(4-pyrrolidin-3-yl-phenyl)-urea hydrochloride To a stirred solution of (RS)-3-{4-[3-(5-chloro-pyridin-2-yl)-ureido]-phenyl}-pyrrolidine-1-carboxylic acid tert-butyl ester (210 mg) in THF (4 ml) was added dropwise a solution of hydrogen chloride in dioxane (1.89 ml, 4 M solution) and the mixture was heated at 60° C. overnight. The mixture was then cooled to 0° C. and the ensuing crystals were collected by filtration, washing with ethyl acetate, and were dried in vacuo at 60° C. to afford (RS)-1-(5-chloro-pyridin-2-yl)-3-(4-pyrrolidin-3-yl-phenyl)-urea hydrochloride (167 mg, 94%) as a beige crystalline solid. MS (ISP): 319.1 ([{$^{37}$Cl}M+H]$^+$), 317.2 ([{$^{35}$Cl}M+H]$^+$).

S8

(RS)-5-Chloro-pyridine-2-carboxylic acid (4-pyrrolidin-3-yl-phenyl)-amide hydrochloride

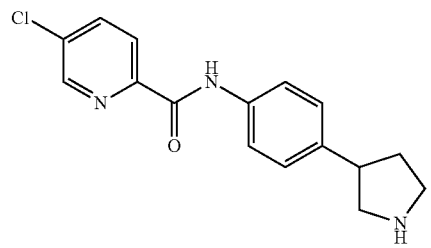 [SMILES: O=C(Nc1ccc(C2CCNC2)cc1)c1ccc(Cl)cn1]

a) (RS)-3-{4-[(5-Chloro-pyridine-2-carbonyl)-amino]-phenyl}-pyrrolidine-1-carboxylic acid tert-butyl ester To a stirred suspension of (RS)-tert-butyl 3-(4-aminophenyl)pyrrolidine-1-carboxylate (200 mg, CAS 908334-28-1) in DMF (10 ml) were added sequentially N-methylmorpholine (0.22 ml), TBTU (490 mg) and 5-chloro-2-pyridine carboxylic acid (180 mg) and the mixture was stirred at room temperature for 90 min. The mixture was then diluted with ethyl acetate and washed sequentially with 1 M aq. hydrochloric acid and with saturated brine. The phases were separated and the organic phase was dried over sodium sulphate and concentrated in vacuo. The residue was purified by column chromatography (SiO$_2$; gradient: heptane/EtOAc) to give (RS)-3-{4-[(5-chloro-pyridine-2-carbonyl)-amino]-phenyl}-pyrrolidine-1-carboxylic acid tert-butyl ester (310 mg, quant.) as a white solid. MS (ISP): 421.3 ([M+NH$_4$]$^+$), 419.2 ([M+NH$_4$]$^+$).

b) (RS)-5-Chloro-pyridine-2-carboxylic acid (4-pyrrolidin-3-yl-phenyl)-amide hydrochloride To a stirred solution of (RS)-3-{4-[(5-chloro-pyridine-2-carbonyl)-amino]-phenyl}-pyrrolidine-1-carboxylic acid tert-butyl ester (310 mg) in THF (6 ml) was added dropwise a solution of hydrogen chloride in dioxane (2.9 ml, 4 M solution) and the mixture was heated at 60° C. overnight. The mixture was then cooled to 0° C. and the ensuing crystals were collected by filtration, washing with diethyl ether, and were dried in vacuo at 60° C. to afford (RS)-5-chloro-pyridine-2-carboxylic acid (4-pyrrolidin-3-yl-phenyl)-amide hydrochloride as a light yellow solid. MS (ISP): 304.2 ([{$^{37}$Cl}M+H]$^+$), 302.3 ([{$^{35}$Cl}M+H]$^+$).

S9

(S)-4-[(S)-1-(4-Fluoro-phenyl)-ethoxymethyl]-4,5-dihydro-oxazol-2-ylamine

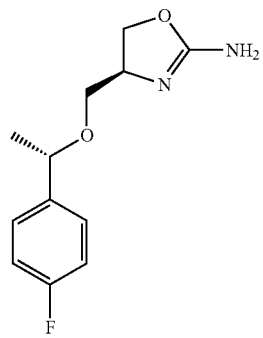 [SMILES: C[C@H](OC[C@H]1COC(N)=N1)c1ccc(F)cc1]

a) 1-((S)-1-Allyloxy-ethyl)-4-fluoro-benzene

To a stirred suspension of sodium hydride (3.14 g, 55% dispersion in oil) in dry DMF (180 ml) under an argon atmosphere was added (S)-1-(4-fluorophenyl)-ethanol (8.41 g, CAS 101219-73-2). Allyl bromide (6.6 ml) was then added dropwise. The reaction mixture was stirred for 30 min at room temperature and was then quenched by addition of water. The mixture was extracted with ethyl acetate twice. The combined organic layers were dried (MgSO$_4$) and concentrated in vacuo. The crude product was purified by column chromatography (SiO$_2$; gradient: heptane/EtOAc) to give 1-((S)-1-allyloxy-ethyl)-4-fluoro-benzene (8.66 g, 80%) as a colourless liquid. $^1$H NMR (300 MHz, CDCl$_3$, δ ppm): 1.43 (d, J=6.6 Hz, 3H), 3.84 (m, 2H), 4.45 (q, J=6.6 Hz, 1H), 5.15 (dd, J$_1$=10.5 Hz, J$_2$=1.8 Hz, 1H), 5.22 (dd, J$_1$=17.4 Hz, J$_2$=1.8 Hz, 1H), 5.89 (m, 1H), 7.03 (m, 2H), 7.29 (m, 2H).

b) (S)-3-[(S)-1-(4-Fluoro-phenyl)-ethoxy]-propane-1,2-diol

AD-MIX-β (62.9 g) was stirred in t-BuOH/H2O 1:1 (440 ml) for 15 min at room temperature and then cooled to 0° C. To this solution was added 1-((S)-1-allyloxy-ethyl)-4-fluoro-benzene (8.00 g). The mixture was stirred for 48 h at 0° C. The reaction mixture was treated with sodium sulfite and stirred for 30 min at 0° C. and at room temperature for 1 day. The solution was extracted with ethyl acetate twice. The combined organic layers were dried (MgSO$_4$) and concentrated in vacuo. The product was purified by column chromatography (SiO$_2$; gradient: heptane/EtOAc 1/1 to 0/1) to give an 80:20 mixture of (S)-3-[(S)-1-(4-fluoro-phenyl)-ethoxy]-propane-1,2-diol & (R)-3-[(S)-1-(4-fluoro-phenyl)-ethoxy]-propane-1,2-diol (8.59 g, 90%) as a light yellow liquid. $^1$H NMR (300 MHz, CDCl$_3$, δ ppm): 1.44 (d, J=6.6 Hz, 3H), 2.1 (b, 1H), 2.6 (b, OH), 3.39 (m, 2H), 3.60 (m, 1H), 3.64 (m, 1H), 3.83 (m, 1H), 4.41 (q, J=6.6 Hz, 1H), 7.03 (m, 2H), 7.27 (m, 2H).

c) (R)-1-(tert-Butyl-dimethyl-silanyloxy)-3-[(S)-1-(4-fluoro-phenyl)-ethoxy]-propan-2-ol To a solution of the 80:20 mixture of (S)-3-[(S)-1-(4-fluoro-phenyl)-ethoxy]-propane-1,2-diol & (R)-3-[(S)-1-(4-fluoro-phenyl)-ethoxy]-propane-1,2-diol (8.40 g) in tetrahydrofuran (84 ml) were added triethylamine (5.74 ml) and 4-dimethylaminopyridine (479 mg). The mixture was cooled to 0° C. and a solution of tert-butyl(chloro)dimethylsilane (6.21 g) in tetrahydrofuran (17 ml) was added dropwise. After 2 hours at 0° C., the reaction mixture was allowed to stir at room temperature for 16 hours. Water was added and the mixture was extracted twice with diethyl ether. The combined organic layers were dried (MgSO$_4$) and concentrated in vacuo to give an 80:20 mixture of (R)-1-(tert-butyl-dimethyl-silanyloxy)-3-[(S)-1-(4-fluoro-phenyl)-ethoxy]-propan-2-ol & (S)-1-(tert-butyl-dimethyl-silanyloxy)-3-[(S)-1-(4-fluoro-phenyl)-ethoxy]-propan-2-ol (12.6 g, 98%) as a yellow liquid. The crude product was used in the next step without further purification.

d) (S)-2-(tert-Butyl-dimethyl-silanyloxy)-1-[(S)-1-(4-fluoro-phenyl)-ethoxymethyl]-ethylamine To a stirred solution of the 80:20 mixture of (R)-1-(tert-butyl-dimethyl-silanyloxy)-3-[(S)-1-(4-fluoro-phenyl)-ethoxy]-propan-2-ol & (S)-1-(tert-butyl-dimethyl-silanyloxy)-3-[(S)-1-(4-fluoro-phenyl)-ethoxy]-propan-2-ol (12.4 g) and triethylamine (6.84 ml) in dichloromethane (60 ml) at 0° C. was added dropwise a solution of methanesulfonyl chloride (3.52 ml) in THF. The mixture was stirred for 1 hour at 0° C. and then water and dichloromethane were added. The aqueous phase was extracted a second time with dichloromethane, and the combined organic layers were washed with brine and dried over MgSO$_4$. The solvent was evaporated and the product was dried under high vacuum. The resulting crude mesylate product (15.5 g) was dissolved in DMF (100 ml) and sodium azide (4.94 g) was added. The reaction mixture was stirred at 100° C. for 16 hours. The reaction was then quenched with water and the mixture was extracted twice with ethyl acetate. The combined organic layers were dried over MgSO$_4$ and concentrated in vacuo. The crude azide product (15.6 g) was dissolved in methanol (160 ml) and 10% palladium on charcoal (1.6 g) was added. The mixture was stirred under an atmosphere of hydrogen at room temperature for 2 hours. The catalyst was removed by filtration through celite and the filtrate was concentrated in vacuo to give an 80:20 mixture of (S)-2-(tert-butyl-dimethyl-silanyloxy)-1-[(S)-1-(4-fluoro-phenyl)-ethoxymethyl]-ethylamine & (R)-2-(tert-butyl-dimethyl-silanyloxy)-1-[(S)-1-(4-fluoro-phenyl)-ethoxymethyl]-ethylamine (14.4 g, 100%) as a yellow liquid which was used in the next step without further purification.

e) (R)-2-Amino-3-[(S)-1-(4-fluoro-phenyl)-ethoxy]-propan-1-ol

To a stirred solution of the 80:20 mixture of (S)-2-(tert-butyl-dimethyl-silanyloxy)-1-[(S)-1-(4-fluoro-phenyl)-ethoxymethyl]-ethylamine & (R)-2-(tert-butyl-dimethyl-silanyloxy)-1-[(S)-1-(4-fluoro-phenyl)-ethoxymethyl]-ethylamine (14.4 g) in THF (150 ml) at 0° C. was added tetrabutylammonium fluoride (22.9 ml, 1 M solution in THF) and the mixture was stirred at room temperature for 18 h. The solvent was evaporated and the crude product was purified by column chromatography (column: Isolute® Flash-NH$_2$ from Separtis; eluent: ethyl acetate) to give an 80:20 mixture of (R)-2-amino-3-[(S)-1-(4-fluoro-phenyl)-ethoxy]-propan-1-ol & (S)-2-amino-3-[(S)-1-(4-fluoro-phenyl)-ethoxy]-propan-1-ol (5.58 g, 60%) as a light yellow liquid. MS (ISP): 214.4 ([M+H]$^+$).

f) (R)-2-Amino-3-[(S)-1-(4-fluoro-phenyl)-ethoxy]-propan-1-ol (R)-hydroxy-phenyl-acetate To a stirred solution of the 80:20 mixture of (R)-2-amino-3-[(S)-1-(4-fluoro-phenyl)-ethoxy]-propan-1-ol & (S)-2-amino-3-[(S)-1-(4-fluoro-phenyl)-ethoxy]-propan-1-ol (2.94 g) in isopropanol (3 ml) was added a solution of D-(−)-mandelic acid (2.10 g) in isopropanol (2 ml). The solvent was evaporated and replaced with ethyl acetate to afford white crystals which were collected by filtration. The crystals were dissolved in hot EtOAc (65 ml) at 80° C. and the mixture was allowed to cool slowly. Crystals appeared on reaching a temperature of 70° C. and the suspension was then stirred at room temperature for 16 h. The crystals were collected by filtration and redissolved in hot EtOAc (80 ml) at 80° C. and the mixture was allowed to cool slowly until cyrstallisation started and then the resulting suspension was stirred at room temperature for 16 h. The crystals were collected by filtration to afford pure (R)-2-amino-3-[(S)-1-(4-fluoro-phenyl)-ethoxy]-propan-1-ol (R)-hydroxy-phenyl-acetate (3.08 g, 61%) as a white solid. $^1$H NMR (300 MHz, DMSO, δ ppm): 1.34 (d, J=6.3 Hz, 3H), 3.13 (m, 1H), 3.23 (m, 1H), 3.37 (m, 4H), 3.83 (m, 1H), 4.46 (q, J=6.3 Hz, 1H), 4.54 (s, 1H), 7.20 (m, 5H), 7.35 (m, 4H).

g) (S)-4-[(S)-1-(4-Fluoro-phenyl)-ethoxymethyl]-4,5-dihydro-oxazol-2-ylamine

A suspension of (R)-2-amino-3-[(S)-1-(4-fluoro-phenyl)-ethoxy]-propan-1-ol (R)-hydroxy-phenyl-acetate in EtOAc was treated with aqueous sodium bicarbonate solution and the mixture was stirred at room temperature until all the solid had dissolved. The phases were separated and the organic layer was dried over MgSO$_4$. The solvent was evaporated to afford (R)-2-amino-3-[(S)-1-(4-fluoro-phenyl)-ethoxy]-propan-1-ol as the free base.

To a stirred solution of (R)-2-amino-3-[(S)-1-(4-fluoro-phenyl)-ethoxy]-propan-1-ol (1.40 g) in THF (80 ml) were added sequentially K$_2$CO$_3$ (1.82 g) and cyanogen bromide (0.83 g). The mixture was stirred at room temperature for 18 hours, then water was added. The mixture was extracted twice with ethyl acetate and the combined organic layers were dried over MgSO$_4$ and evaporated over Isolute® Flash-NH$_2$ silica gel. Chromatography (column: Isolute® Flash-NH$_2$ from Separtis; eluent: heptane/ethyl acetate=25:75) yielded the title compound as a white solid, (1.15 g, 73%). MS (ISP): 239.0 ([M+H]$^+$).

S10

5-Chloro-pyrimidine-2-carboxylic acid {4-[2-((S)-2-amino-4,5-dihydro-oxazol-4-yl)-ethyl]-phenyl}-amide

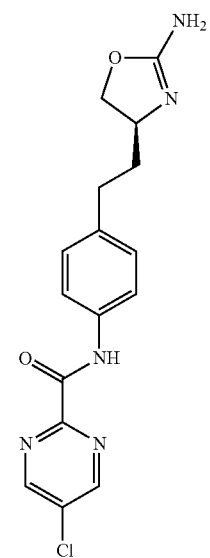 [SMILES: NC1=N[C@@H](CCc2ccc(NC(=O)c3ncc(Cl)cn3)cc2)CO1]

The title compound was obtained in analogy to example S3 using 5-chloropyrimidine-2-carboxylic acid (CAS 38275-61-5) instead of 4-chlorobenzoic acid in step c). White solid. MS (ISP): 348.3 ([{$^{37}$Cl}M+H]$^+$), 346.1 ([{$^{35}$Cl}M+H]$^+$).

S11

N-{4-[2-((S)-2-Amino-4,5-dihydro-oxazol-4-yl)-ethyl]-phenyl}-4-chloro-benzamide

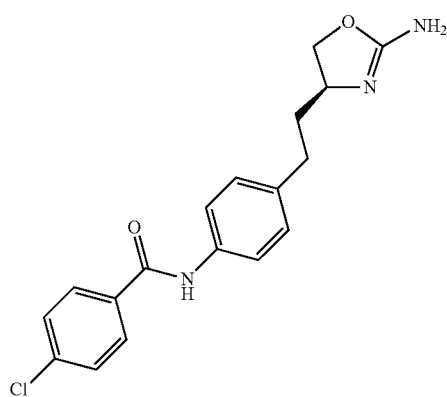 [SMILES: NC1=N[C@@H](CCc2ccc(NC(=O)c3ccc(Cl)cc3)cc2)CO1]

a) S-2,2-Dimethyl-4-[(E)-2-(4-nitro-phenyl)-vinyl]-oxazolidine-3-carboxylic acid tert-butyl ester To a stirred solution of diisopropylamine (1.81 ml) in THF (50 ml) cooled to −78° C. was added dropwise a solution of n-butyllithium in hexane (8.05 ml, 1.6 M). The cooling bath was removed and the reaction mixture was allowed to warm up to 10° C. before being re-cooled to −78° C. A solution of (4-nitro-benzyl)-phosphonic acid diethyl ester (2.71 g, CAS 2609-49-6) in THF (60 ml) was then added dropwise and the reaction mixture stirred at −78° C. for 1 hour. A solution of (R)-4-formyl-2,2-dimethyl-oxazolidine-3-carboxylic acid tert-butyl ester (2.50 g, CAS 95715-87-0) in THF (50 ml) was then added dropwise over 30 min and the mixture was then allowed to warm to room temperature over 90 min. The mixture was then diluted with ethyl acetate and acidified by addition of 1 N aq. hydrochloric acid. The mixture was then washed sequentially with water and with saturated brine. The organic phase was separated and was dried over sodium sulphate and concentrated in vacuo. The reside was purified by column chromatography (SiO$_2$; gradient: heptane/EtOAc) to give (S)-2,2-dimethyl-4-[(E)-2-(4-nitro-phenyl)-vinyl]-oxazolidine-3-carboxylic acid tert-butyl ester (2.21 g, 64%) as a yellow oil. MS (EI): 333 ([M-CH$_3$]$^+$), 292 ([M-C$_4$H$_8$]$^+$), 277 ([M-CH$_3$—C$_4$H$_8$]$^+$), 57 ([C$_4$H$_9$]$^+$).

b) (S)-4-[2-4-Amino-phenyl)-ethyl]-2,2-dimethyl-oxazolidine-3-carboxylic acid tert-butyl ester To a stirred suspension of (S)-2,2-dimethyl-4-[(E)-2-(4-nitro-phenyl)-vinyl]-oxazolidine-3-carboxylic acid tert-butyl ester (2.08 g) in methanol (140 ml) were added ammonium formate (5.66 g) and palladium on charcoal (0.51 g, 10 wt %) and the mixture was heated at 60° C. for 90 min. The mixture was then cooled to room temperature, filtered through celite and the filtrate was concentrated in vacuo. The residue was purified by column chromatography (SiO$_2$; gradient: heptane/EtOAc) to give (S)-4-[2-(4-amino-phenyl)-ethyl]-2,2-dimethyl-oxazolidine-3-carboxylic acid tert-butyl ester (1.58 g, 82%) as a yellow oil. MS (ISP): 321.4 ([M+H]$^+$).

c) (S)-4-{2-[4-(4-Chloro-benzoylamino)-phenyl]-ethyl}-2,2-dimethyl-oxazolidine-3-carboxylic acid tert-butyl ester To a stirred solution of (S)-4-[2-(4-amino-phenyl)-ethyl]-2,2-dimethyl-oxazolidine-3-carboxylic acid tert-butyl ester (20) in THF (4 ml) were added 4-chlorobenzoic acid (147 mg), N-methylmorpholine (0.27 ml) and TBTU (401 mg). The reaction mixture was heated to 50° C. and stirred for 16 h. The reaction mixture was then concentrated in vacuo and the residue was purified by flash column chromatography (SiO$_2$; gradient: EtOAc/heptane) to afford (S)-4-{2-[4-(4-chloro-benzoylamino)-phenyl]-ethyl}-2,2-dimethyl-oxazolidine-3-carboxylic acid tert-butyl ester as a white solid (254 mg, 89%). MS (ISP): 478.3 ([{$^{37}$Cl}M+NH$_4$]$^+$), 476.3 ([{$^{35}$Cl}M+NH$_4$]$^+$), 405.4 ([{$^{37}$Cl}M+H—C$_4$H$_8$]$^+$), 403.2 ([{$^{35}$Cl}M+H—C$_4$H$_8$]$^+$).

d) N-[4-((S)-3-Amino-4-hydroxy-butyl)-phenyl]-4-chloro-benzamide

To a solution of (S)-4-{2-[4-(4-chloro-benzoylamino)-phenyl]-ethyl}-2,2-dimethyl-oxazolidine-3-carboxylic acid tert-butyl ester (438 mg) in acetonitrile (5 ml) were added water (4 ml) and trifluoroacetic acid (0.29 ml). The mixture was heated at 80° C. for 4.5 h. The mixture was then cooled to room temperature and poured into 1 M aq. NaOH and extracted twice with EtOAc/THF. The combined organic layers were washed with brine, dried over Na$_2$SO$_4$, filtered and concentrated in vacuo to afford N-[4-((S)-3-amino-4-hydroxy-butyl)-phenyl]-4-chloro-benzamide (255 mg, 84%) a white solid. MS (ISP): 321.2 ([{$^{37}$Cl}M+H]$^+$), 319.2 ([{$^{35}$Cl}M+H]).

e) N-{4-[2-((S)-2-Amino-4,5-dihydro-oxazol-4-yl)-ethyl]-phenyl}-4-chloro-benzamide To a stirred suspension of N-[4-((S)-3-Amino-4-hydroxy-butyl)-phenyl]-4-chloro-benzamide (250 mg) and sodium acetate (124 mg) in methanol (10 ml) was added dropwise a solution of cyanogen bromide (100 mg) in methanol (3 ml). The resulting pale yellow solution was then stirred at room temperature for 16 h. The reaction mixture was poured into 1 N aq. NaOH and extracted twice with dichloromethane/THF. The combined organic layers were washed with sat. aq. NaCl, dried over Na$_2$SO$_4$, filtered and concentrated in vacuo. The crude material was purified by flash chromatography (silica gel; eluant: 0% to 100% EtOAc in heptane, then 0% to 30% MeOH in EtOAc) to afford N-{4-[2-((S)-2-amino-4,5-dihydro-oxazol-4-yl)-ethyl]-phenyl}-4-chloro-benzamide (150 mg, 56%) as a white solid. MS (ISP): 346.1 ([{$^{37}$Cl}M+H]$^+$), 344.2 ([{$^{35}$Cl}M+H]$^+$).

S12

(R)-2-Chloro-6-methyl-N-(4-(morpholin-2-yl)phenyl)isonicotinamide hydrochloride

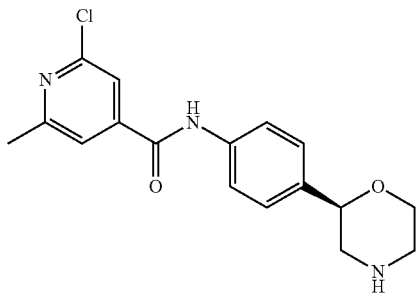 [SMILES: Cc1cc(C(=O)Nc2ccc([C@@H]3CNCCO3)cc2)cc(Cl)n1]

The title compound was obtained in analogy to example S4 using (R)-2-(4-bromo-phenyl)-morpholine instead of (S)-2-(4-bromo-phenyl)-morpholine in step b) and 2-chloro-6-methylisonicotinic acid (CAS 25462-85-5) instead of 6-(2,2,2-trifluoroethoxy)nicotinic acid in step e). Light yellow solid. MS (ISP): 334.1 ([{$^{37}$Cl}M+H]$^+$), 332.1 ([{$^{35}$Cl}M+H]$^+$).

S13

(S)—N-(4-(Morpholin-2-yl)phenyl)-6-(2,2,2-trifluoroethoxy)nicotinamide hydrochloride

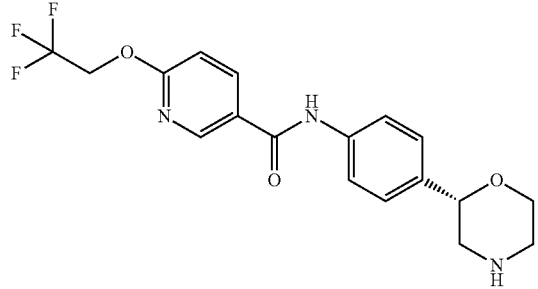 [SMILES: O=C(Nc1ccc([C@H]2CNCCO2)cc1)c1ccc(OCC(F)(F)F)nc1]

a) (S)-2-(4-Bromophenyl)morpholine

The enantiomers of (RS)-2-(4-bromo-phenyl)-morpholine (2.27 g, CAS-1131220-82-0) were separated using chiral HPLC (column: Chiralpak IA, 8×32 cm; eluent: n-heptane/ethanol (1:11) containing 0.1% DEA) affording:
(S)-2-(4-Bromo-phenyl)-morpholine: collected from 7.6 min to 9.4 min.
Yield 0.97 g (42.9%) with 97.4% ee
(R)-2-(4-Bromo-phenyl)-morpholine: collected from 9.8 min to 13.9 min
Yield 0.99 g (43.6%) with 97.4% ee b) (S)-tert-Butyl 2-(4-bromophenyl)morpholine-4-carboxylate (S)-2-(4-Bromo-phenyl)-morpholine (36.3 g) and N,N-diisopropylethylamine (31.4 ml) in THF (360 ml) were treated with di-tert-butyl dicarbonate (39.3 g). The reaction mixture was stirred for 17 h at room temperature, then concentrated in vacuo, diluted with ethyl acetate, washed with 1 M aq. citric acid (2×100 ml), dried over magnesium sulfate, filtered and concentrated in vacuo. The crude material was crystallized from hexane to afford (S)-tert-butyl 2-(4-bromophenyl)morpholine-4-carboxylate (47.1 g, 92%) as an off-white solid. MS (ISP): 344.1 ([M+H]$^+$).

c) (S)-tert-Butyl 2-(4-(diphenylmethyleneamino)phenyl)morpholine-4-carboxylate (S)-tert-Butyl 2-(4-bromophenyl)morpholine-4-carboxylate (47 g), diphenylmethanimine (29.9 g), BINAP (6.41 g) and Pd$_2$(dba)$_3$ (3.14 g) were dissolved under Argon in dry and de-aerated toluene (940 ml) and treated with sodium tert-butoxide (18.5 g). The dark brown mixture was stirred at 90° C. for 18 h. The yellow/brown reaction mixture was diluted with toluene (700 ml), cooled to room temperature and extracted twice with water. The organic layer was separated, dried over magnesium sulfate and concentrated in vacuo. The crude product was diluted with 300 ml hexane, stirred for 1 h and filtered off, leading to an orange solid (68 g) which was purified by column chromatography (silicagel, 20% ethylacetate/heptane). The combined and concentrated fractions were suspended in hexane, stirred for 17 h, filtered off and dried in vacuo to yield (S)-tert-butyl 2-(4-(diphenylmethyleneamino)phenyl)morpholine-4-carboxylate (54.1 g, 89%) as a yellow solid. MS (ISP): 443.3 ([M+H]$^+$).

d) (S)-tert-Butyl 2-(4-aminophenyl)morpholine-4-carboxylate

A suspension of (S)-tert-Butyl 2-(4-(diphenylmethyleneamino)phenyl)morpholine-4-carboxylate (54.1 g), ammonium formate (116 g) and 5% palladium on charcoal (6.5 g) in methanol (930 ml) was stirred at 60° C. for 2 h. The reaction mixture was filtered and concentrated in vacuo. The residue was dissolved in ethyl acetate and water. The organic phase was extracted twice with 0.5 M aq. HCl. The combined aqueous phases were basified with 2 M aq. NaOH and extracted twice with dichloromethane. The organic phases were dried over magnesium sulfate, filtered and dried in vacuo to yield (S)-tert-butyl 2-(4-aminophenyl)morpholine-4-carboxylate (31.95 g, 94%) as an off-white solid. MS (ISP): 279.1 ([M+H]$^+$).

e) (S)-tert-Butyl 2-(4-(6-(2,2,2-trifluoroethoxy)nicotinamido)phenyl)morpholine-4-carboxylate To a stirred suspension of (S)-tert-butyl 2-(4-aminophenyl)morpholine-4-carboxylate (1.5 g) in THF (75 ml) were added sequentially N-methylmorpholine (1.78 ml), HBTU (3.07 g) and 6-(2,2,2-trifluoroethoxy)nicotinic acid (1.63 g) and the mixture was stirred at room temperature for 17 h. The suspension was diluted with EtOAc and washed sequentially with 0.5 M aq. HCl, sat. aq. NaHCO$_3$ and saturated brine. The organic layer was dried over MgSO$_4$, filtered and concentrated in vacuo. The crude product was purified by recrystallisation from heptane/EtOAc (1:1) to give (S)-tert-butyl 2-(4-(6-(2,2,2-trifluoroethoxy)nicotinamido)phenyl)morpholine-4-carboxylate (2.11 g, 81%) as a white solid. MS (ISP): 482.1 ([M+H]$^+$).

f) (S)—N-(4-(Morpholin-2-yl)phenyl)-6-(2,2,2-trifluoroethoxy)nicotinamide hydrochloride To a stirred suspension of (S)-tert-butyl 2-(4-(6-(2,2,2-trifluoroethoxy)nicotinamido)phenyl)morpholine-4-carboxylate (2.11 g) in dioxane (8 ml) was added dropwise a solution of hydrogen chloride in dioxane (16.7 ml, 4 M solution) and the mixture was heated at 60° C. for 2 hours. The reaction mixture was cooled to room temperature, diluted with dioxane, and the crystalline product was collected by filtration, washing with Et$_2$O. The product was dried in vacuo to afford (S)—N-(4-(morpholin-2-yl)phenyl)-6-(2,2,2-trifluoroethoxy)nicotinamide hydrochloride (1.75 g, 94%) as a light yellow solid. MS (ISP): 382.2 ([M+H]$^+$).

S14

(S)—N-(4-(Morpholin-2-yl)phenyl)-2-(trifluoromethyl)isonicotinamide hydrochloride

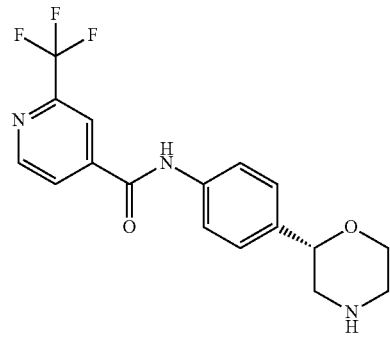 [SMILES: O=C(Nc1ccc([C@H]2CNCCO2)cc1)c1ccnc(C(F)(F)F)c1]

The title compound was obtained in analogy to example S4 using 2-(trifluoromethyl)isonicotinic acid (CAS 131747-41-6) instead of 6-(2,2,2-trifluoroethoxy)nicotinic acid in step e). Off-white solid. MS (ISP): 352.3 ([M+H]$^+$).

S15

(S)-1-(4-Fluorobenzyl)-3-(4-(morpholin-2-yl)phenyl)urea hydrochloride

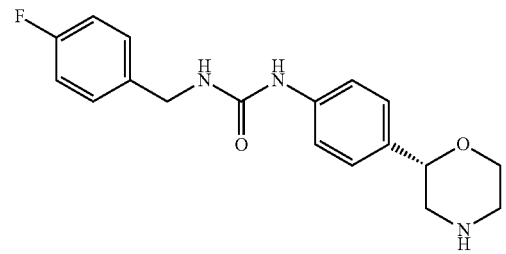 [SMILES: O=C(NCc1ccc(F)cc1)Nc1ccc([C@H]2CNCCO2)cc1]

a) (S)-tert-Butyl 2-(4-(3-(4-fluorobenzyl)ureido) phenyl)morpholine-4-carboxylate To a stirred solution of (S)-tert-butyl 2-(4-aminophenyl) morpholine-4-carboxylate (100 mg) in DMF (3.5 ml) were added sequentially triethylamine (62 µl) and 1-fluoro-4-(isocyanatomethyl)benzene (58.4 µl) and the mixture was stirred at 60° C. for 17 h. The suspension was cooled to room temperature, then diluted with water and extracted twice with EtOAc. The combined organic phases were washed sequentially with water and saturated brine. The organic layer was dried over $MgSO_4$, filtered and concentrated in vacuo. The residue was purified was purified by flash chromatography (silica gel; gradient: EtOAc/heptane) to afford (S)-tert-butyl 2-(4-(3-(4-fluorobenzyl)ureido)phenyl)morpholine-4-carboxylate (164 mg, quant.) as a white solid. MS (ISP): 374.0 ($[M+H-C_4H_8]^+$).

b) (S)-1-(4-Fluorobenzyl)-3-(4-(morpholin-2-yl) phenyl)urea hydrochloride

To a stirred suspension of (S)-tert-butyl 2-(4-(3-(4-fluorobenzyl)ureido)phenyl) morpholine-4-carboxylate (163 mg) in THF (9 ml) was added dropwise a solution of hydrogen chloride in dioxane (1.42 ml, 4 M solution) and the mixture was heated at 60° C. for 6 hours. The reaction mixture was cooled to room temperature, diluted with EtOAc, and the crystalline product was collected by filtration, washing with $Et_2O$. The product was dried in vacuo to afford (S)-1-(4-fluorobenzyl)-3-(4-(morpholin-2-yl)phenyl)urea hydrochloride (101 mg, 73%) as a white solid. MS (ISP): 330.1 ($[M+H]^+$).

S16

(S)-1-(3-Cyanophenyl)-3-(4-(morpholin-2-yl)phenyl)urea hydrochloride

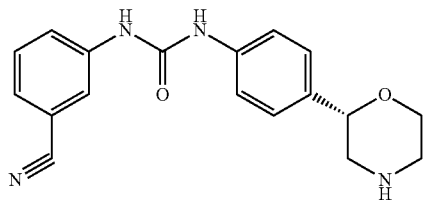 [SMILES: N#Cc1cccc(NC(=O)Nc2ccc([C@H]3CNCCO3)cc2)c1]

The title compound was obtained in analogy to example S7 using 3-isocyanatobenzonitrile (CAS 16413-26-6) instead of 1-fluoro-4-(isocyanatomethyl)benzene in step a). Off-white solid. MS (ISP): MS (ISP): 323.2 ($[M+H]^+$).

S17

(S)-6-Chloro-N-(4-(morpholin-2-yl)phenyl)nicotinamide hydrochloride

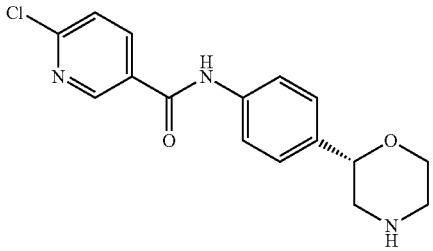 [SMILES: O=C(Nc1ccc([C@H]2CNCCO2)cc1)c1ccc(Cl)nc1]

The title compound was obtained in analogy to example S4 using 6-chloronicotinic acid (CAS 5326-23-8) instead of 6-(2,2,2-trifluoroethoxy)nicotinic acid in step e). Off-white solid. MS (ISP): MS (ISP): 320.1 ($[\{^{37}Cl\}M+H]^+$), 318.1 ($[\{^{35}Cl\}M+H]^+$).

In Vitro Functional Activity of TAAR1 Agonists at Mouse TAAR1 Receptor

Recombinant HEK293 cells expressing the mouse TAAR1 were grown at 37° C. and 5% CO2/95% air in 250 ml Falcon culture flasks in 30 ml culture medium. The cell culture medium contained DMEM high glucose, fetal calf serum (10%, heat inactivated for 30 min at 56° C.), geneticin G418 (500 µg/ml), and penicillin/streptomycin (1%). Cells were harvested when 80-90% confluent. Then culture medium was then removed from the culture flasks, cells washed once with 5 ml of PBS. After removing the wash solution, 5 ml of trypsin/EDTA solution were added for 5 min at 37° C. Afterwards, 45 ml of culture medium was added to the 5 ml detached cell solution and the total 50 ml transferred into a 50 ml Falcon tube (ref: 2070), the tube was centrifuged at 1300 rpm for 3 min at RT and the culture medium removed. The cell pellet was resuspended in fresh culture medium and brought to 5×10 E5 cells per milliliter. Then the cells were plated in 96-well Plate (BIOCOAT 6640 from Becton Dickinson) with a multipipette (100 µl/well, 50 000 cells/well) and incubated 20 h at 37° C.

cAMP Assay:

The cell culture medium was removed and the cells washed once with PBS. 50 µl of PBS (AMIMED Endotoxine free: 8-05F00-1) with 1 mM IBMX were added and the cells allowed to incubate for 30 min at 37° C. and 5% CO2/95% air. Then 50 µl of a (e.g.) 20 µM compound solution or 50 µl of a 50% beta-PEA stimulation concentration in PBS (AMIMED Endotoxine free) with 1 mM IBMX were added and the cells incubated for 30 min at 37° C. as above again. After the incubation the cells were lysed with 50 µl of the 3× Detection Mix solution containing Ru-cAMP, Alexa700-cAMP Ab and lysis buffer for at least 60 min (better 2 h) at RT under strong shaking. The fluorescence is measured on the NanoScan (10M reader) (Ex. 456 nm, Em. 630 & 700 nm).

The compounds show an $EC_{50}$ value (µM) at mouse TAAR1 in the range of <0.01 µM as shown in the table below. Efficacy values (% eff.) are relative to phenylethylamine having 100% agonistic activity.

| Example | $EC_{50}$ (µM) % efficacy |
|---------|---------------------------|
| S1      | 0.0020                    |
|         | 90%                       |
| S2      | 0.0018                    |
|         | 65%                       |
| S3      | 0.0013                    |
|         | 67%                       |
| S4      | 0.0033                    |
|         | 65%                       |
| S5      | 0.0016                    |
|         | 51%                       |
| S6      | 0.0014                    |
|         | 78%                       |
| S7      | 0.0008                    |
|         | 57%                       |
| S8      | 0.0074                    |
|         | 65%                       |
| S9      | 0.0017                    |
|         | 99%                       |
| S10     | 0.0016                    |
|         | 32%                       |
| S11     | 0.0001                    |
|         | 45%                       |

-continued

| Example | EC$_{50}$ (μM)<br>% efficacy |
|---|---|
| S12 | 0.0031<br>69% |
| S13 | 0.0016<br>54% |
| S14 | 0.0046<br>55% |
| S15 | 0.0006<br>40% |
| S16 | 0.0004<br>60% |
| S17 | 0.0018<br>39% |

Antipsychotic-Like Activity of TAAR1 Agonists Additive and Synergistic to the Marketed Antipsychotic Olanzapine in Two Animal Models Indicative for Psychosis Additive Effect of TAAR1 Agonists and Olanzapine in Cocaine-Induced Locomotion Test in Mice Activation of TAAR1 was shown to down-modulate dopaminergic neurotransmission, whereas inhibition of TAAR1 was shown to enhance it (Lindemann et al., 2008; Bradaia et al., 2009). Data from cocaine- and L-687414 (benzyloxyamine)-induced hyperlocomotor activity tests in mice indicate that TAAR1 agonists have potential antipsychotic-like activity.

At doses that had modest effects on baseline locomotor activity, S2 significantly antagonized cocaine-induced hyperlocomotor activity at 1 and 3 mg/kg p.o. in mice. In addition, partially active doses of S2 (0.3 mg/kg, p.o.) and olanzapine (0.3 mg/kg, p.o.), when combined, fully reversed the hyperlocomotion induced by cocaine (FIG. 1a). This indicates that S2 may have an additive effect on the marketed antipsychotic olanzapine.

Figure 1B:
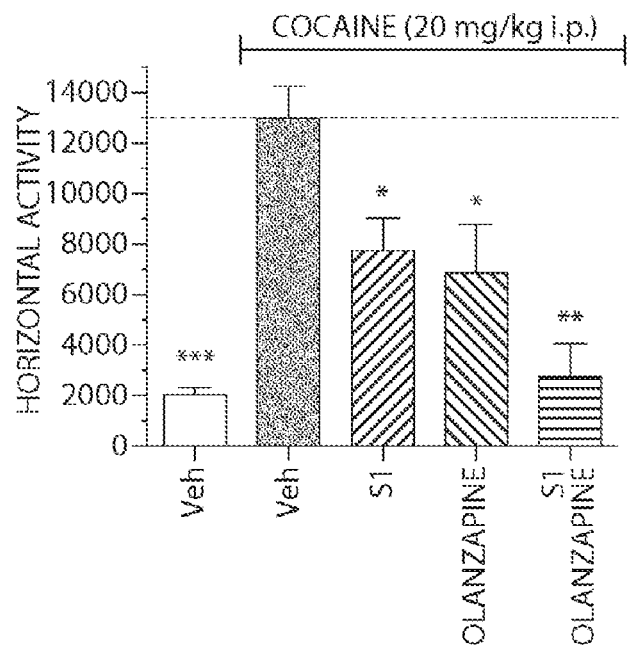

It was also observed that, while doses of S1 (0.1 mg/kg, p.o.) and olanzapine (0.3 mg/kg, p.o.) partially antagonized cocaine-induced locomotor activity when tested separately, a full reversal of cocaine-induced hyperlocomotor activity was observed when these compounds were combined (FIG. 1b).

This indicates that S1 has an additive effect on the marketed antipsychotic olanzapine, supporting its potential as add-on therapy to marketed antipsychotics.

FIG. 1

Effects on Cocaine-Induced Locomotion in Mice a) Doses of S1 (0.1 mg/kg p.o.) and olanzapine (0.3 mg/kg p.o.), that partially antagonized cocaine-induced hyperlocomotor activity when tested alone, showed a normalization effect when combined. * $p \leq 0.05$,  $p \leq 0.01$, * $p \leq 0.002$ versus "vehicle and cocaine" group.

b) Doses of S2 (0.3 mg/kg p.o.) and olanzapine (0.3 mg/kg p.o.), that partially antagonized cocaine-induced hyperlocomotor activity when tested alone, showed a normalization effect when combined. * $p \leq 0.05$,  $p \leq 0.01$, * $p \leq 0.002$ versus "vehicle and cocaine" group.

Figure 2:
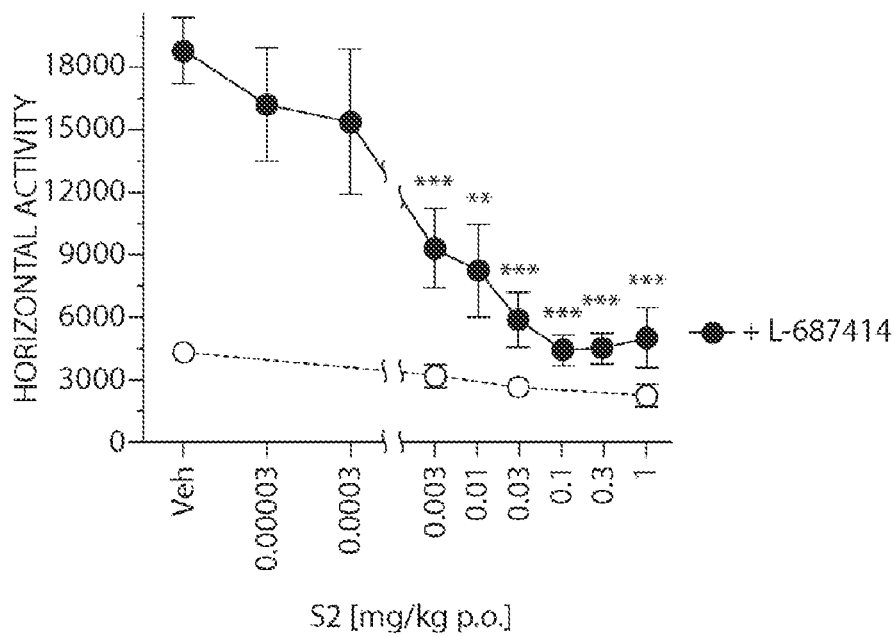
FIG. 2 illustrates the effects of TAAR1 agonist on L-687414-induced locomotion in mice.

Synergistic Effect of TAAR1 Agonist and Olanzapine in L-687414-Induced Locomotion Test in Mice To address its potential effect on the glutamatergic system, S2 (0.00003-1 mg/kg, p.o.) was tested in the acute procedure of L-687414 (N-hydroxy-3-amino-4-methyl-pyrrolidin-2-one, NMDA receptor antagonist acting at the glycine site)-induced hyperlocomotion in mice, where it dose-dependently antagonized L-687414, with significance in the dose range of 0.003 to 1 mg/kg, p.o. (FIG. 2).

FIG. 2

Effects of TAAR1 Agonist on L-687414-Induced Locomotion in Mice

L-687414-Induced Locomotion: S2 (0.00003-1 mg/kg p.o.) fully antagonized L-687414-induced hyperlocomotor activity from 0.003 to 1 mg/kg (filled circles). * $p \leq 0.05$,  $p \leq 0.01$, * $p \leq 0.001$ versus vehicle (empty circles).

Figure 3:
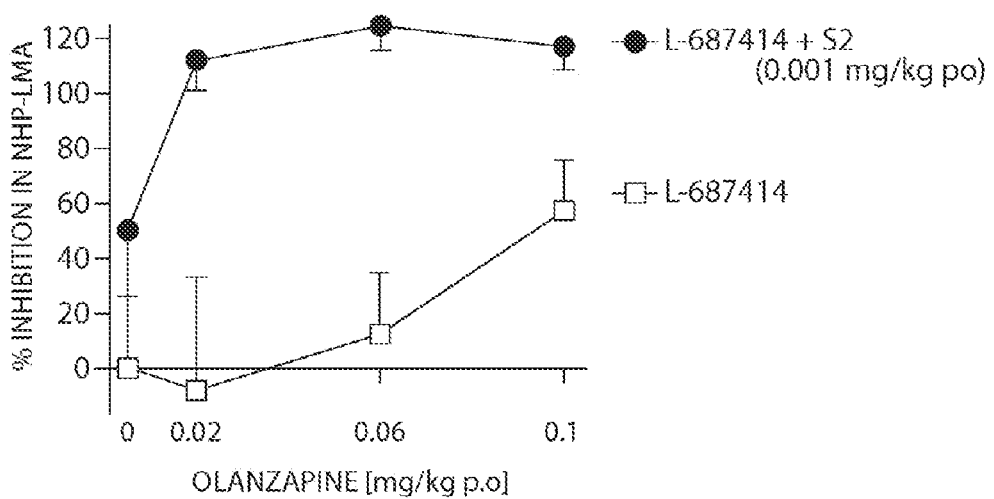
FIG. 3 illustrates synergism with olanzapine in L-687414-induced locomotion in mice.

Furtheron, a partially active dose of the TAAR1 agonist S2 (0.001 mg/kg, p.o.; grey bar in FIG. 2) was added to increasing doses of olanzapine (0-0.1 mg/kg, p.o.). As shown in FIG. 3, partially active dose of S2 (0.001 mg/kg, p.o.) combined with non-active doses of olazapine (0.02-0.06 mg/kg, p.o.) fully antagonized L-687414-induced locomotor activity, indicating that the TAAR1 agonist and olanzapine show synergistic effects in this mouse model indicative for schizophrenia.

FIG. 3

Synergism with Olanzapine in L-687414-Induced Locomotion in Mice

L-687414-Induced Locomotion: S2 (0.001 mg/kg, p.o.) combined with increasing doses of olazapine (0-0.1 mg/kg, p.o.) fully antagonized L-687414-induced hyperlocomotor activity at 0.02 and 0.06 mg/kg olazapine. * $p \leq 0.05$,  $p \leq 0.01$, * $p \leq 0.001$ L-687414+S2 vs L-687414 group alone.

Acute Effect of TAAR1 Agonists on Oral Glucose Tolerance Test (oGTT) in Regular Male C57Bl6 Mice An oral glucose tolerance test (oGTT) was performed in C57Bl6 mice to address potential anti-diabetic effects of TAAR1 agonists. Male C57BL/6J mice (Charles River Laboratories, Lyon, France) were stratified into groups of 8 mice according to body weight. The evening before the animals received 1 g food, this corresponds to a fasting period of about 10 hours. At the experiment day the animals were treated with TAAR1 agonists or placebo (0.3% Tween 80) 45 minutes prior to an oral glucose challenge of 2 g/kg. The main readout was blood glucose measured with Accu-Chek Aviva. In parallel blood samples were taken for insulin determination.

Figure 4A:
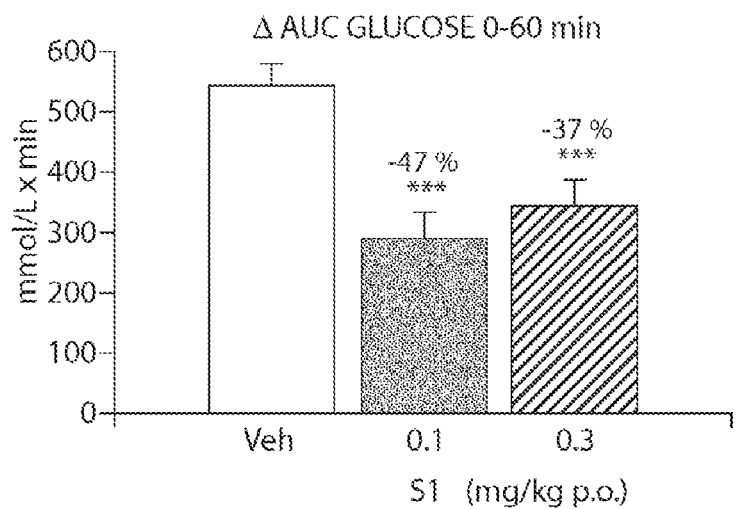
FIG. 4 illustrates the effects of S1 on glucose and insulin AUC in oGTT in mice.
Figure 4B:
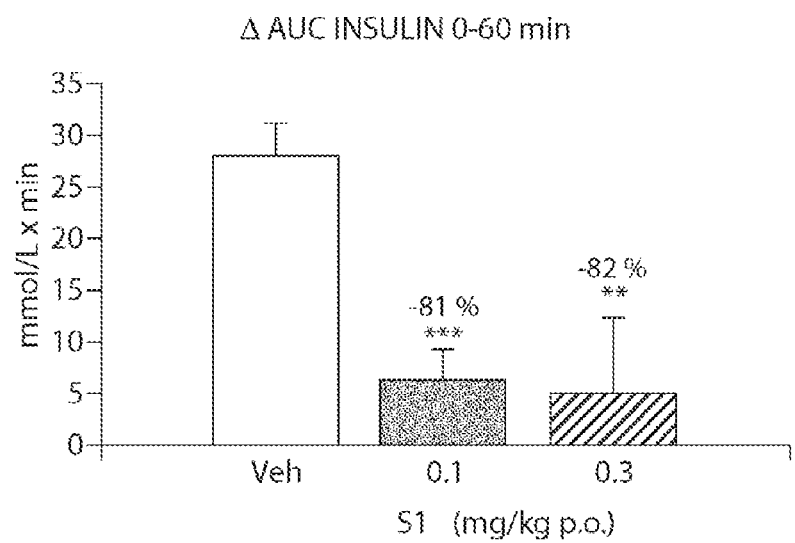
Figure 5A:
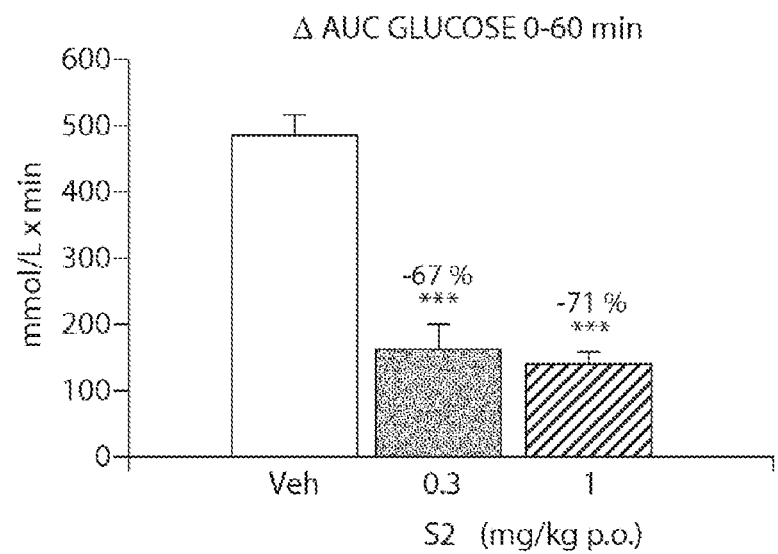
FIG. 5 illustrates the effects of S2 on glucose and insulin AUC in oGTT in mice.
Figure 5B:
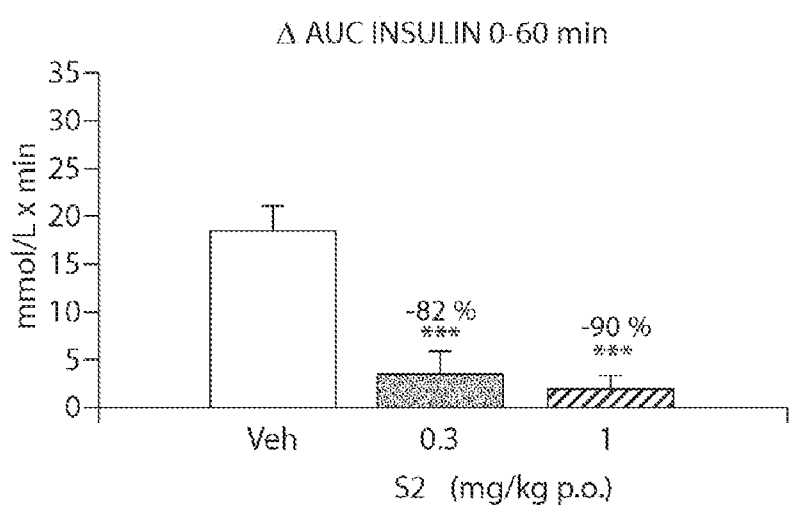
Figure 6A:
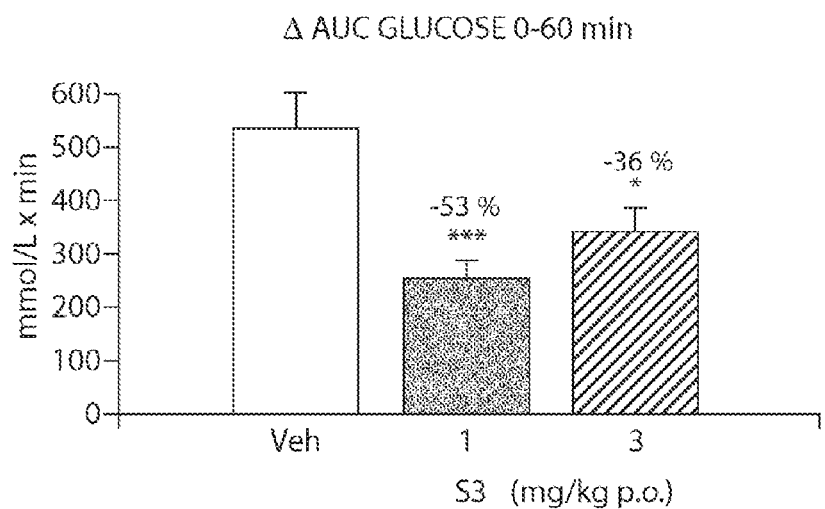
FIG. 6 illustrates the effects of S3 on glucose and insulin AUC in oGTT in mice.
Figure 6B:
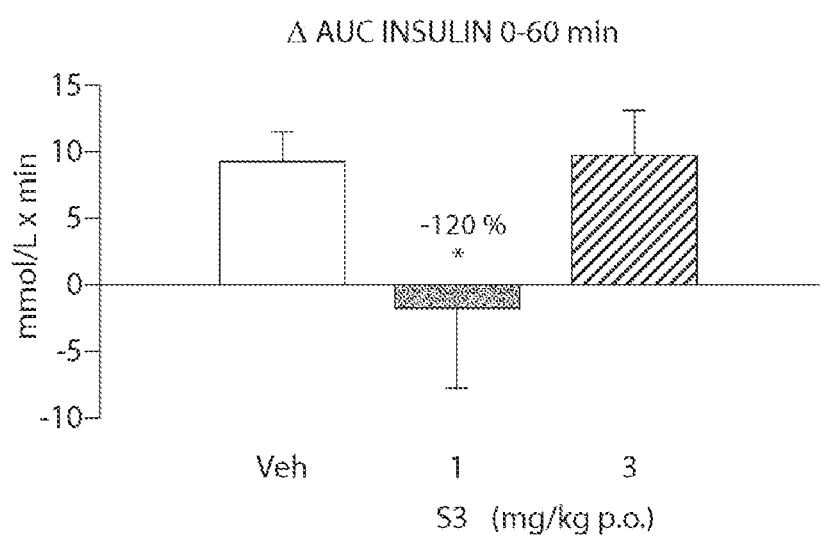
Figure 7A:
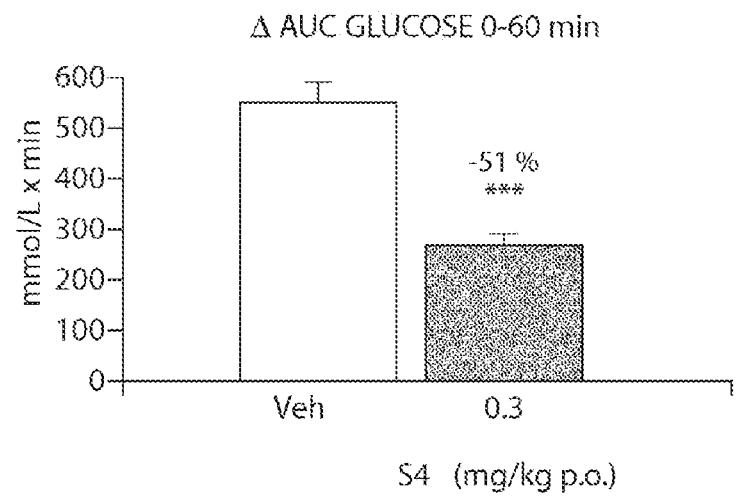
FIG. 7 illustrates the effects of S4 on glucose and insulin AUC in oGTT in mice.
Figure 7B:
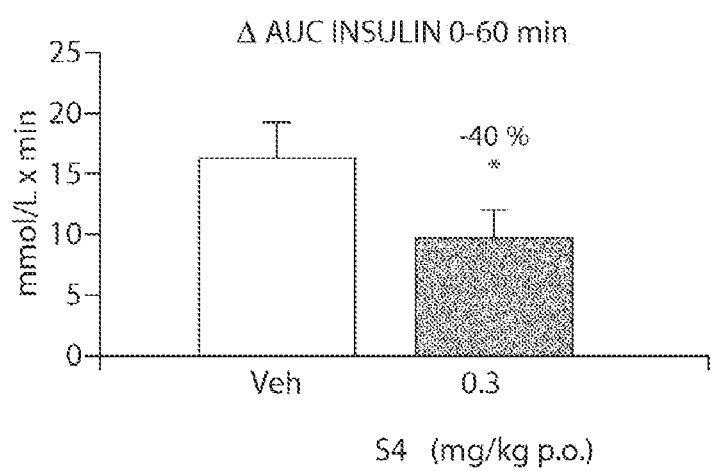
Figure 8:
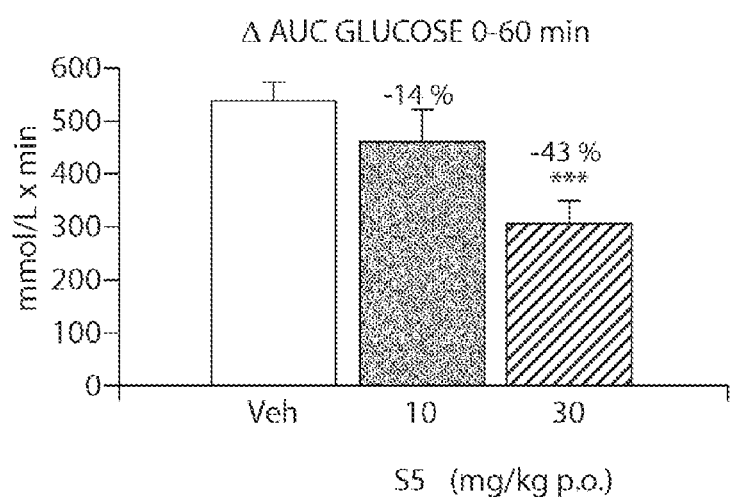
FIG. 8 illustrates the effects of S5 on glucose AUC in oGTT in mice.
Figure 9A:
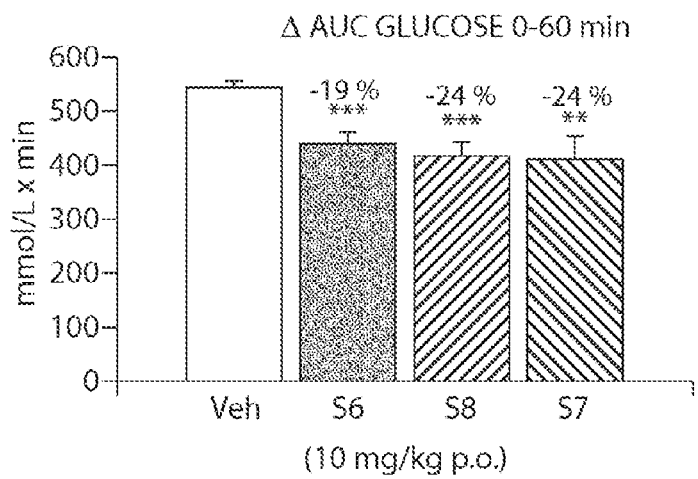
FIG. 9 illustrates the effects of S6, S7, and S8 (10 mg/kg, p.o. each) on glucose AUC in oGTT in mice.
Figure 9B:
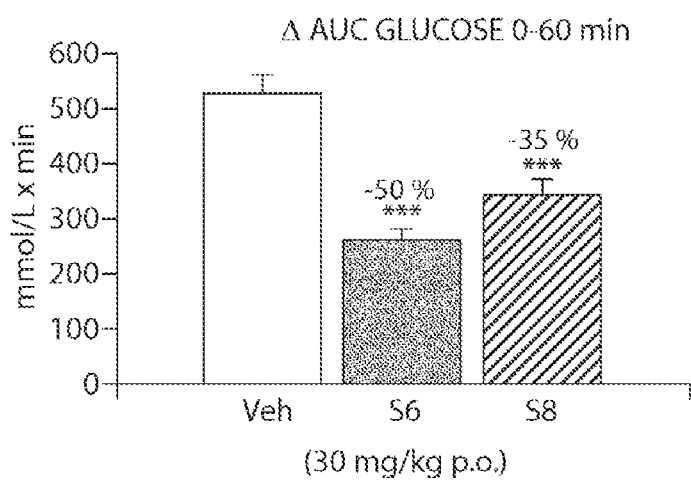
Figure 10A:
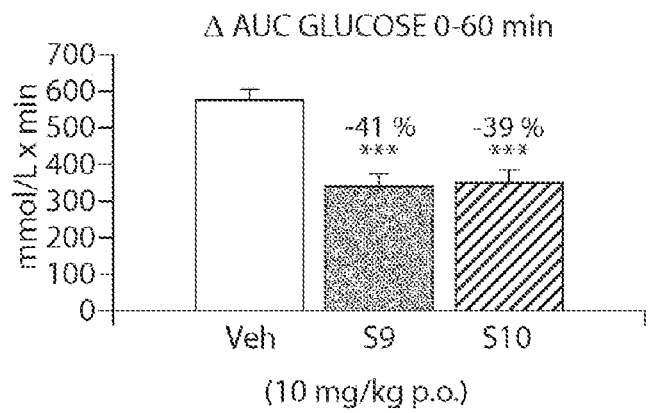
FIG. 10 illustrates the effects of S9, S10, and S11 on glucose AUC in oGTT in mice.
Figure 10B:
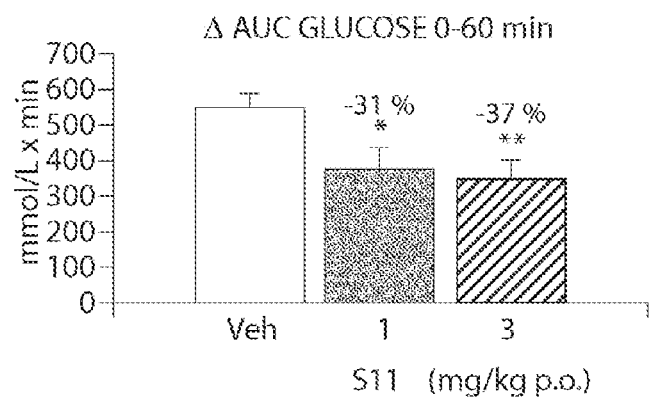
Figure 11A:
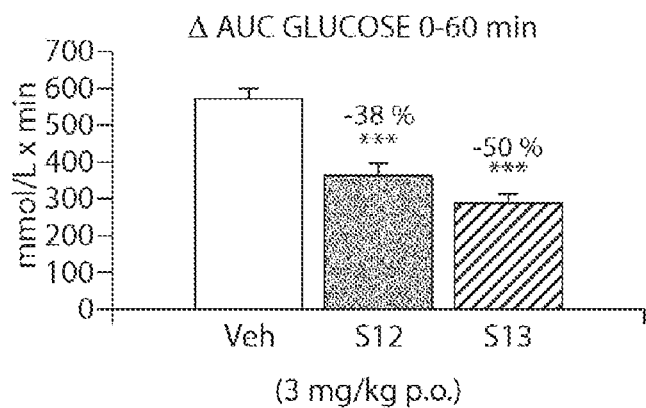
FIG. 11 illustrates the effects of S12, S13, S14, S15, and S16 on glucose AUC in oGTT in mice.
Figure 11B:
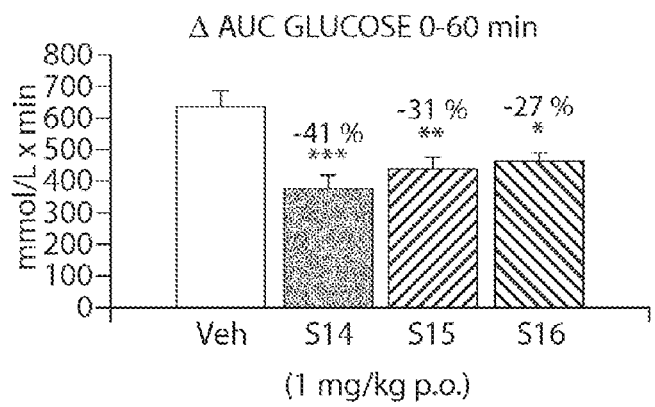
Figure 12:
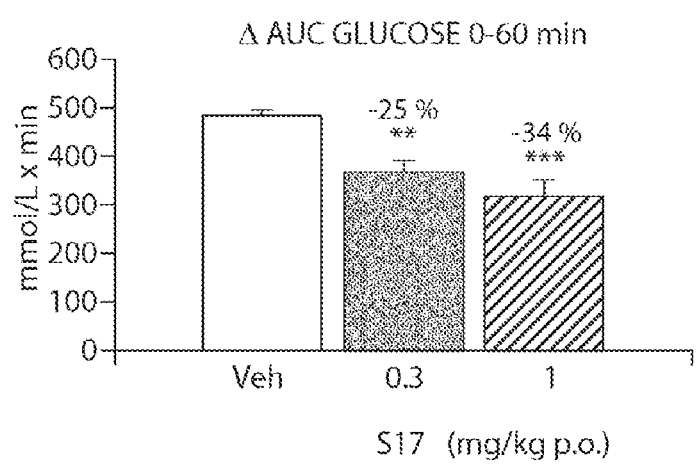
FIG. 12 illustrates the effects of S17 (0.3 and 1 mg/kg, p.o.) on glucose AUC in oGTT in mice.

S1 significantly lowered blood glucose excursion at 0.1 and 0.3 mg/kg, p.o. compared to vehicle after glucose challenge (FIG. 4a). At the same time, insulin excursion was significantly lower upon TAAR1 agonist administration compared to vehicle treatment (FIG. 4b). No effect on fasting glucose levels were observed using S1. As metabolic syndrome has a high prevalence in schizophrenia, an anti-diabetic effect is envisioned to have a positive impact on schizophrenic patients.

FIG. 4

Effect of S1 on Glucose and Insulin AUC in oGTT in Mice

S1 (0.1, 0.3 mg/kg p.o.) markedly lowered (a) glucose and (b) insulin AUC (0-60 min) during oGTT in mice. Results are shown as mean±SEM. Statistics: Anova followed by Dunett's post hoc test,  $p \leq 0.01$, * $p \leq 0.001$ versus vehicle (Veh) group; n=8/group.

Several additional TAAR1 agonists (S2-8) with various levels of efficacy (51-90% compared to beta-phenylethylamine) were tested in the oGTT and all showed a significant effect in reducing glucose AUC and whereas tested in reducing insulin AUC (FIGS. 5-9)

FIG. 5

Effect of S2 on Glucose and Insulin AUC in oGTT in Mice

S2 (0.3, 1 mg/kg, p.o.) markedly lowered (a) glucose and (b) insulin AUC (0-60 min) during oGTT in mice. Results are shown as mean±SEM. Statistics: Anova followed by Dunett's post hoc test, *** $p \leq 0.001$ versus vehicle (Veh) group; n=8/group.

FIG. 6

Effect of S3 on Glucose and Insulin AUC in oGTT in Mice

S3 (1, 3 mg/kg p.o.) markedly lowered (a) glucose and (b) insulin AUC (0-60 min) during oGTT in mice. Results are shown as mean±SEM. Statistics: Anova followed by Dunett's post hoc test, * p≤0.05, *** p≤0.001 versus vehicle (Veh) group; n=8/group.

FIG. 7

Effect of S4 on Glucose and Insulin AUC in oGTT in Mice

S4 (0.3 mg/kg, p.o.) markedly lowered (a) glucose and (b) insulin AUC (0-60 min) during oGTT in mice. Results are shown as mean±SEM. Statistics: Anova followed by Dunett's post hoc test, * p≤0.05, *** p≤0.001 versus vehicle (Veh) group; n=8/group.

FIG. 8

Effect of S5 on Glucose AUC in oGTT in Mice

S5 (30 mg/kg, p.o.) markedly lowered glucose AUC (0-60 min) during oGTT in mice. Results are shown as mean±SEM. Statistics: Anova followed by Dunett's post hoc test, *** p≤0.001 versus vehicle group; n=8/group.

FIG. 9

Effects of S6, S7 and S8 (10 mg/kg, p.o., each) on Glucose AUC in oGTT in Mice

S6 (10 and 30 mg/kg, p.o.), S7 (10 mg/kg, p.o.), and S8 (10 and 30 mg/kg, p.o.) markedly lowered glucose AUC (0-60 min) during oGTT in mice. Results are shown as mean±SEM. Statistics: Anova followed by Dunett's post hoc test,  p≤0.01, * p≤0.001 versus vehicle group; n=8/group.

FIG. 10

Effects of S9, S10 and S11 on Glucose AUC in oGTT in Mice a) S9 (10 mg/kg, p.o.) and S10 (10 mg/kg, p.o.) as well as b) S11 (1 and 3 mg/kg, p.o.) markedly lowered glucose AUC (0-60 min) during oGTT in mice. Results are shown as mean±SEM. Statistics: Anova followed by Dunett's post hoc test, * p≤0.05,  p≤0.01, * p≤0.001 versus vehicle group; n=8/group.

FIG. 11

Effects of S12, S13, S14, S15 and S16 on Glucose AUC in oGTT in Mice a) S12 and S13 (3 mg/kg, p.o., each) as well b) S14, S15 and S16 (1 mg/kg, p.o., each) markedly lowered glucose AUC (0-60 min) during oGTT in mice. Results are shown as mean±SEM. Statistics: Anova followed by Dunett's post hoc test, * p≤0.05,  p≤0.01, * p≤0.001 versus vehicle group; n=8/group.

FIG. 12

Effects of S17 (0.3 and 1 mg/kg, p.o.) on Glucose AUC in oGTT in Mice a) S17 (0.3 and 1 mg/kg, p.o.) markedly lowered glucose AUC (0-60 min) during oGTT in mice. Results are shown as mean±SEM. Statistics: Anova followed by Dunett's post hoc test,  p≤0.01, * p≤0.001 versus vehicle group; n=8/group.

TAAR1 Agonists Reduce Weight Gain Increase in Normal Rats and Normalize Weight Gain Increase Induced by the Antipsychotic Drug Olanzapine.

Many antipsychotic drugs induce weight gain in patients with schizophrenia. Since weight gain can lead to serious health complications and diseases such as diabetes, it is crucial to evaluate promising, newer antipsychotic compounds in animals for their propensity to alter weight.

A 14-day treatment regimen was used in female Sprague-Dawley rats with S2 and olanzapine, a clinically-used antipsychotic drug that is know to produce weight gain. Along with body weight measurement, magnetic resonance (MR) relaxometry was employed to determine, in a noninvasive manner, fat mass composition in the animals.

Figure 13A:
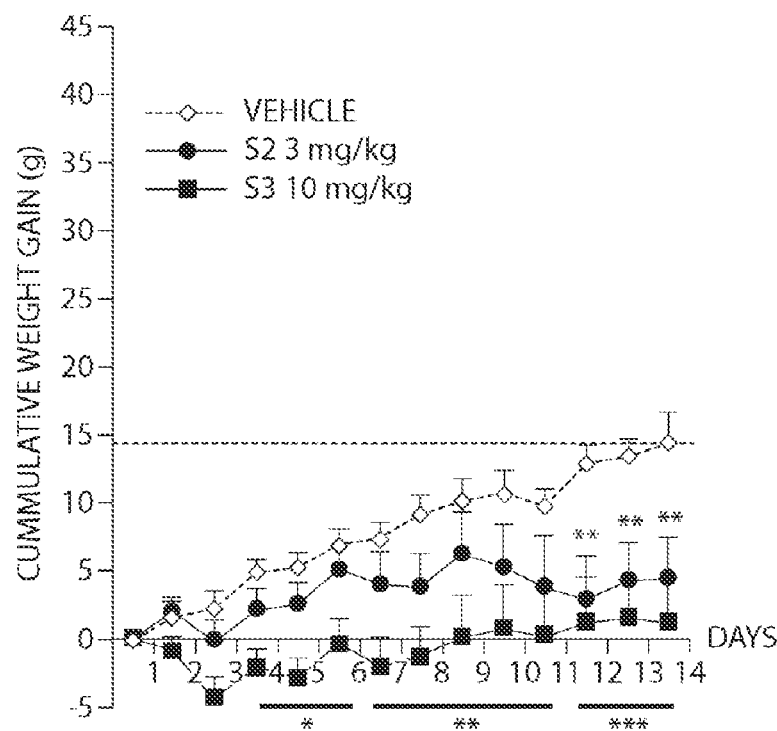
FIG. 13 illustrates the effects of S2 on cumulative weight gain in rats.
Figure 13B:
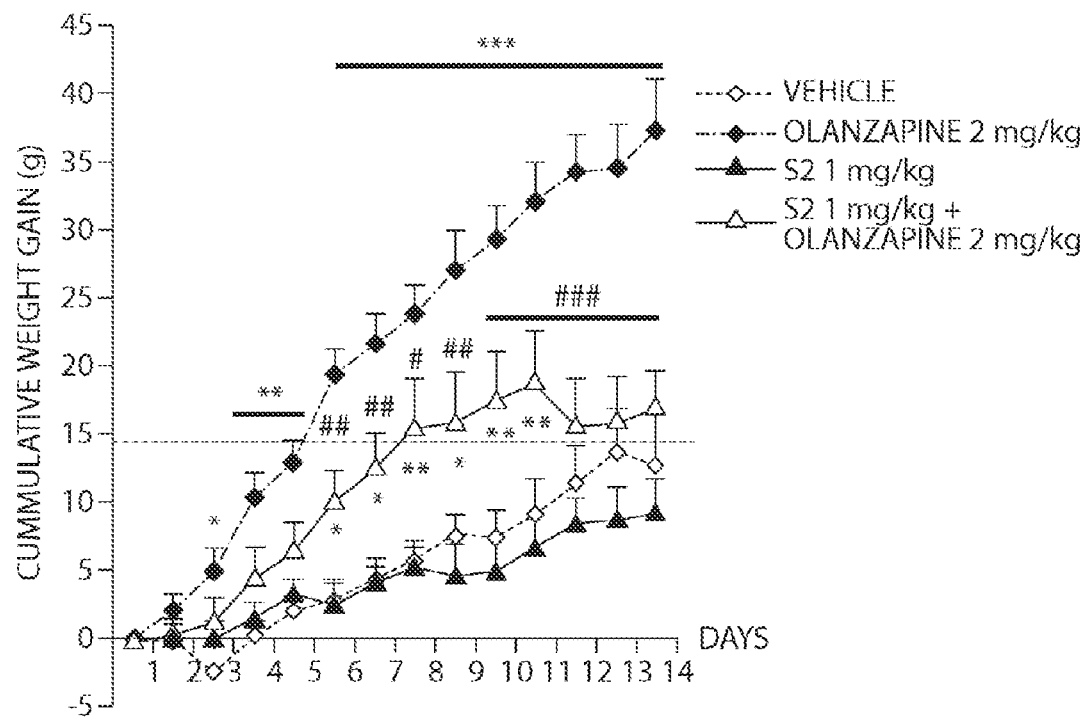
Figure 14A:
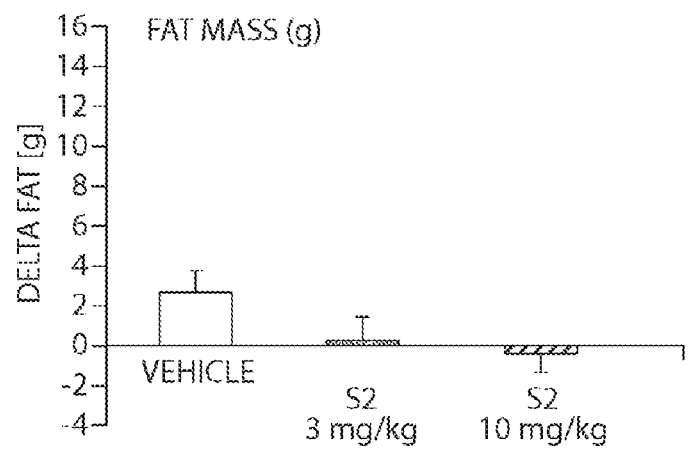
FIG. 14 illustrates the effects of S2 on fat mass content in rats.
Figure 14B:
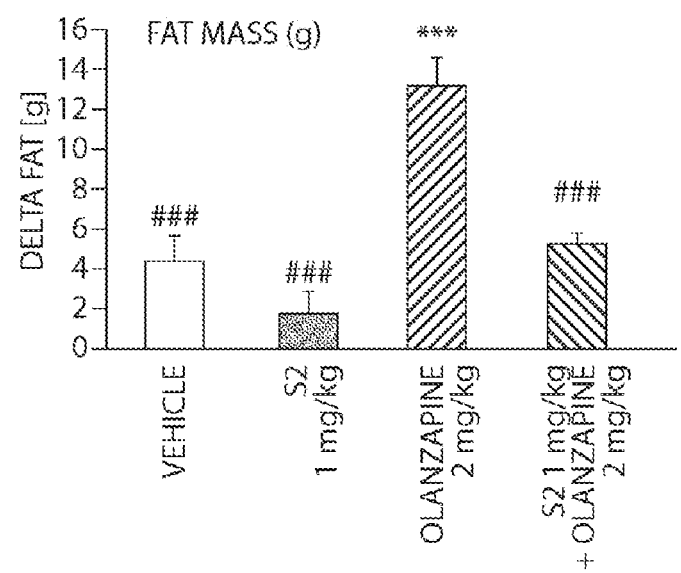
Figure 14C:
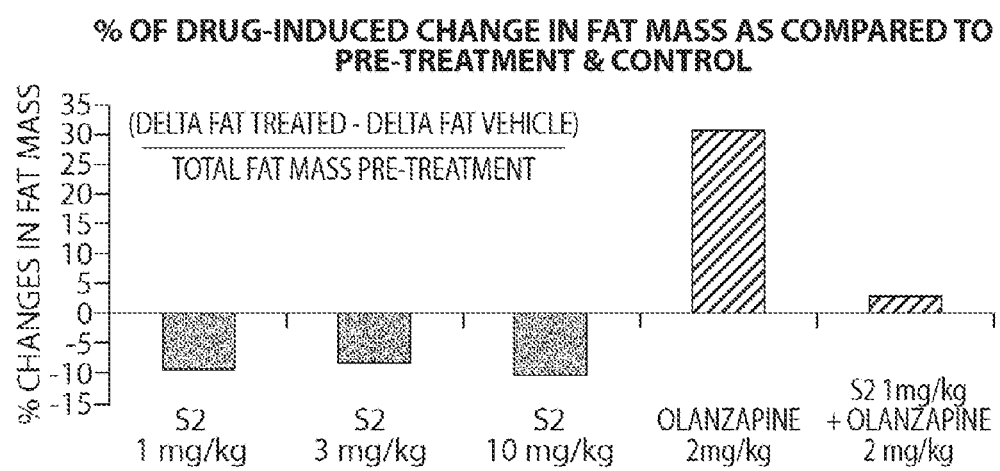

The results show that S2 at 3 and 10 mg/kg p.o. reduced weight gain (FIG. 13a), fat mass (FIG. 14a, 14c) and food intake (Table 1) as compared to vehicle-treated animals, without inducing weight loss when compared to pre-treatment values. No significant effect was measured at 1 mg/kg p.o. (FIG. 13b, 14b, Table 1). In addition, S2 (1 mg/kg p.o.) combined with olanzapine (2 mg/kg p.o.) reduced the increase in weight gain, fat mass content and food intake measured in olanzapine-treated rats (FIG. 13b, 14b, Table 1).

This indicates that S2 does not induce weight gain when administered alone, and can inhibit the weight gain induced by the marketed antipsychotic olanzapine.

FIG. 13

Effects of S2 on Cumulative Weight Gain in Rats a) S2 at 3 and 10 mg/kg, but not at 1 mg/kg p.o. reduced weight gain in female Sprague-Dawley rats (contrasts of linear trends in S2 groups vs linear trend in vehicle group, p=0.0024 at 3 mg/kg and p=0.012 at 10 mg/kg). (b) S2 (1 mg/kg p.o.) combined with olanzapine (2 mg/kg p.o.) normalized the olanzapine-induced weight gain (linear trends olanzapine vs vehicle, p=4.6E-10; S2/olanzapine vs vehicle, p=0.41). Between-group comparisons at each time point: t-test, * p≤0.05,  p≤0.01, * p≤0.001 versus vehicle; # p≤0.05, ## p≤0.01, ### p≤0.001 versus olanzapine group; n=8/group.

FIG. 14

Effects of S2 on Fat Mass Content in Rats

S2 (1 mg/kg p.o.) combined with olanzapine (2 mg/kg p.o.) normalized the olanzapine-induced fat mass increase in female Sprague-Dawley rats. No significant effect of S2 alone was measured when compared to the vehicle group. Dunett's test * p≤0.05,  p≤0.01, * p≤0.001 versus vehicle; # p≤0.05, ## p≤0.01, ### p≤0.001 versus olanzapine group; n=8/group.

TABLE 1

Effects of S2 on cumulative food intake in rats
S2 (1 mg/kg p.o.) combined with olanzapine (2 mg/kg p.o.) normalized the olanzapine-induced increase in food intake. A significant reduction in food intake was measured in S2-treated rats at 10 mg/kg; n = 8/group.

| Treatment | Cumulative food intake ± SEM (g) | Dunnett's test p value |
|---|---|---|
| Study 1 | | |
| Vehicle | 254.9 ± 7.0 | |
| S2 (3 mg/kg) | 233.8 ± 7.4 | 0.18 |
| S2 (10 mg/kg) | 217.0 ± 7.3 | 0.0050 |
| Study 2 | | |
| Vehicle | 263.4 ± 3.8 | |
| S2 (1 mg/kg) | 248.8 ± 5.0 | 0.45 |
| Olanzapine (2 mg/kg) | 301.6 ± 8.6 | 0.0034 |
| S2 (1 mg/kg) & Olanzapine (2 mg/kg) | 268.6 ± 8.6 | 0.96 |

Olanzapine and the compounds of formulas I, I-1, II and II-1 and the pharmaceutically acceptable salts can be used as medicaments, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formulas I, I-1, II and II-1 can be processed with pharmaceutically inert, inorganic or organic carriers for the production of pharmaceutical compositions. Lactose, corn starch, cellulose or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides pharmaceutical compositions containing olanzapine and a compound of formulas I, I-1, II and II-1 or a pharmaceutically acceptable salt thereof and a therapeutically inert carrier, and provides a process for their production, which comprises bringing one or more compounds of formulas I, I-1, II and II-1 and olanzapine and/or pharmaceutically acceptable acid addition salts and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of olanzapine and a compound of general formulas I, I-1, II and II-1 or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | mg/tablet | | | |
| Item Ingredients | 5 mg | 25 mg | 100 mg | 500 mg |
| 1. Compound of formula I | 5 | 25 | 100 | 500 |
| 2. Lactose Anhydrous DTG | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 1 | 1 | 1 |
| Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | mg/capsule | | | |
| Item Ingredients | 5 mg | 25 mg | 100 mg | 500 mg |
| 1. Compound of formula I | 5 | 25 | 100 | 500 |
| 2. Hydrous Lactose | 159 | 123 | 148 | — |
| 3. Corn Starch | 25 | 35 | 40 | 70 |
| 4. Talc | 10 | 15 | 10 | 25 |
| 5. Magnesium Stearate | 1 | 2 | 2 | 5 |
| Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

| Olanzapine Tablet Formulation | | | | |
|---|---|---|---|---|
| | mg/capsule | | | |
| Item Ingredients | 2.5 mg | 7.5 mg | 15 mg | 20 mg |
| 1. Olanzapine | 2.5 | 7.5 | 15.0 | 20.0 |
| 2. Lactose monohydrate | 89.0 | 84.0 | 76.5 | 71.5 |
| 3. Hyprolose | 7.5 | 7.5 | 7.5 | 7.5 |
| 4. Crospovidon | 4.5 | 4.5 | 4.5 | 4.5 |
| 5. Microcrystalline Cellulose | 45.0 | 45.0 | 45.0 | 45.0 |
| 6. Magnesiumstearate | 1.5 | 1.5 | 1.5 | 1.5 |
| Total | 150.0 | 150.0 | 150.0 | 150.0 |

Manufacturing Procedure
1. Mix items 1 to 5 and granulate with purified water.
2. Dry the granules at 50° C.
3. Pass the granules through suitable milling equipment.
4. Add item 6 and mix for three minutes; compress on a suitable press.

| Combination formulation | | | |
|---|---|---|---|
| | mg/capsule | | |
| Item Ingredients Compound of formula I/Olanzapine | 5/2.5 | 25/2.5 | 100/15 mg |
| 1. Compound of formula I | 5.00 | 25.00 | 100.00 |
| 2. Olanzapine | 2.50 | 2.50 | 15.00 |
| 3. Lactose monohydrate | 166.25 | 146.25 | 58.75 |
| 4. Povidon K30 | 12.50 | 12.50 | 12.50 |
| 5. Croscarmellose Sodium | 7.50 | 7.50 | 7.50 |
| 6. Microcrystalline Cellulose | 50.00 | 50.00 | 50.00 |
| 7. Magnesiumstearate | 1.25 | 1.25 | 1.25 |
| 8. Talc | 5.00 | 5.00 | 5.00 |
| Total | 250.00 | 250.00 | 250.00 |

Manufacturing Procedure
1. Mix items 1 to 6 and granulate with purified water.
2. Dry the granules at 50° C.
3. Pass the granules through suitable milling equipment.
4. Add item 7 and 8 and mix for three minutes; compress on a suitable press.

The invention claimed is:
1. A combination comprising a therapeutically effective amount of each of olanzapine and,
(S)-4-(3-fluoro-2-methyl-phenyl)-4,5-dihydro-oxazol-2-ylamine, or a pharmaceutically suitable acid addition additional salt thereof, said combination being charac- terized by a reduced incidence of the metabolic syndrome associated with the administration of atypical antipsychotic medications.

2. A pharmaceutical composition comprising a combination of olanzapine and
(S)-4-(3-fluoro-2-methyl-phenyl)-4,5-dihydro-oxazol-2-ylamine or a pharmaceutically suitable acid addition salt thereof and one or more pharmaceutically acceptable excipients, said combination being characterized by a reduced incidence of metabolic syndrome associated with the administration of atypical antipsychotic medications.

* * * * *